United States Patent
He et al.

(10) Patent No.: US 12,098,127 B2
(45) Date of Patent: Sep. 24, 2024

(54) SALT FORM OF ESTROGEN RECEPTOR DOWNREGULATOR, CRYSTALLINE FORM THEREOF, AND PREPARATION METHOD THEREFOR

(71) Applicants: LUOXIN PHARMACEUTICAL (SHANGHAI) CO., LTD., Shanghai (CN); SHANDONG LUOXIN PHARMACEUTICAL GROUP STOCK CO., LTD., Shandong (CN)

(72) Inventors: Huijun He, Shanghai (CN); Shenyi Shi, Shanghai (CN); Jianyu Lu, Shanghai (CN); Charles Z. Ding, Shanghai (CN); Lihong Hu, Shanghai (CN); Bin Shi, Shanghai (CN); Wenqian Yang, Shanghai (CN); Jiaqiang Dong, Shanghai (CN); Tie-Lin Wang, Shanghai (CN)

(73) Assignees: LUOXIN PHARMACEUTICAL (SHANGHAI) CO., LTD., Shanghai (CN); SHANDONG LUOXIN PHARMACEUTICAL GROUP STOCK CO., LTD., Shandong (CN)

(*) Notice: Subject to any disclaimer, the term of this patent is extended or adjusted under 35 U.S.C. 154(b) by 719 days.

(21) Appl. No.: 17/295,878

(22) PCT Filed: Oct. 17, 2019

(86) PCT No.: PCT/CN2019/111624
§ 371 (c)(1),
(2) Date: May 21, 2021

(87) PCT Pub. No.: WO2020/108154
PCT Pub. Date: Jun. 4, 2020

(65) Prior Publication Data
US 2022/0017463 A1 Jan. 20, 2022

(30) Foreign Application Priority Data
Nov. 28, 2018 (CN) .......................... 201811434915.8

(51) Int. Cl.
*C07D 209/30* (2006.01)

(52) U.S. Cl.
CPC ........ *C07D 209/30* (2013.01); *C07B 2200/13* (2013.01)

(58) Field of Classification Search
None
See application file for complete search history.

(56) References Cited

U.S. PATENT DOCUMENTS

| 8,455,534 B2 | 6/2013 | Smith et al. |
| 9,855,270 B2 | 1/2018 | Hager et al. |
| 10,519,143 B2 * | 12/2019 | Lu ........................... A61P 43/00 |
| 11,034,653 B2 * | 6/2021 | He ....................... C07D 209/18 |
| 2019/0106414 A1 | 4/2019 | Lu et al. |

FOREIGN PATENT DOCUMENTS

| CN | 103189361 A | 7/2013 |
| CN | 106488767 A | 3/2017 |
| WO | 2012037411 A2 | 3/2012 |
| WO | 2016023847 A1 | 2/2016 |
| WO | 2016201356 A1 | 12/2016 |
| WO | 2017162206 A1 | 9/2017 |
| WO | 2018064476 A1 | 4/2018 |
| WO | 2019057201 A1 | 3/2019 |

OTHER PUBLICATIONS

Morissette et al, Advanced Drug Delivery Reviews, vol. 56, pp. 275-300 (Year: 2004).*
Jul. 27, 2022 extended European Search Report issued in European Patent Application No. 19888746.5.
Aulton M E (Ed) Ed—Aulton M E (Ed) 2: "Pharmaceutical Preformulation", Dec. 25, 2001 (Dec. 25, 2001), Pharmaceutics. The Science of Dosage Form Design Ed 2, Churchill Livigstone, pp. 115-118.
Aug. 8, 2023 the first Office Action issued in Japanese Patent Application No. 2021-530238.
Nov. 24, 2023 Chinese First Office Action issued in Chinese Patent Application No. 2019800784255.
Jan. 15, 2020 International Search Report issued in International Patent Application No. PCT/CN2019/111624.

(Continued)

*Primary Examiner* — Zinna Northington Davis
(74) *Attorney, Agent, or Firm* — Houston Beshining Law Office PLLC; Liangang Ye

(57) ABSTRACT

Provided are a salt form of an estrogen receptor downregulator, a crystalline form thereof, and a preparation method therefor

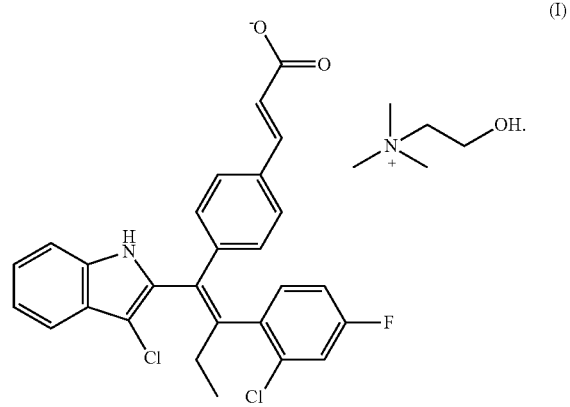

(I)

10 Claims, 12 Drawing Sheets

(56) References Cited

OTHER PUBLICATIONS

Jan. 15, 2020 Written Opinion of the International Searching Authority issued in International Patent Application No. PCT/CN2019/111624.
Priority document CN201811434915.8 filed Nov. 28, 2018.

* cited by examiner

SALT FORM OF ESTROGEN RECEPTOR DOWNREGULATOR, CRYSTALLINE FORM THEREOF, AND PREPARATION METHOD THEREFOR

The present application is a National Stage of International Application No. PCT/CN2019/111624, filed on Oct. 17, 2019, which claims priority of the Chinese Patent Application No. CN201811434915.8 filed on Nov. 28, 2018. The contents of which are incorporated herein by reference in their entirety.

TECHNICAL FIELD

The present disclosure relates to salt forms of estrogen receptor down-regulator, crystalline forms thereof, and processes of preparation therefor, and the use of the salt and crystal forms in the preparation of a drug for treating breast cancer.

BACKGROUND ARTS

According to the statistics of WHO, breast cancer has become the second most prevalent cancer in the world and has the highest incidence among women. After years of research, the role of the estrogen-estrogen receptor signaling pathway in breast cancer development has already been identified; and the estrogen receptor (ER) has also been developed into the most important biomarker for breast cancer. Taking estrogen receptor expression as a discriminative index, breast cancer can be divided into estrogen receptor-positive breast cancer and estrogen receptor-negative breast cancer; wherein estrogen receptor-positive breast cancer accounts for more than 70% of the total number of breast cancer patients.

Endocrine Therapy (ET) targeting the estrogen-estrogen receptor signaling pathway in breast cancer cells has become the first choice for treating estrogen receptor-positive breast cancer because of its minimal harm and significant effect. Endocrine therapy mainly includes the following three treatment methods: ovarian suppression therapy, aromatase inhibitor (AI), and selective estrogen receptor modulator (SERM). Due to its unsatisfactory efficacy and low patient satisfaction, the ovarian suppression therapy is less commonly used than the other two treatment methods. Early aromatase inhibitors (first and second generation) had low target selectivity and large toxic and side effects. After many years of research, the third-generation aromatase inhibitors have been widely used since their selectivity has been greatly improved, which solved the problem of the early aromatase inhibitors. Among them, letrozole and the like have been used as first-line drugs for the treatment of estrogen receptor-positive breast cancer. Selective estrogen receptor modulators (SERMs) directly act on estrogen receptors to block this signaling pathway, which has a significant effect and a long history of application. Among them, tamoxifen is the most representative selective estrogen receptor modulator. As a first-line drug recommended for priority use, tamoxifen has shown significant clinical efficacy in the prevention and treatment of estrogen receptor-positive breast cancer.

Although the aromatase inhibitor letrozole and the selective estrogen receptor modulator tamoxifen have shown good efficacy in the treatment of estrogen receptor-positive breast cancer, with the application of the two types of drugs, the drug resistance problem of estrogen receptor-positive breast cancer to aromatase inhibitors and selective estrogen receptor modulators has also become increasingly prominent. A large amount of studies has shown that the resistance mechanisms of breast cancer to these two hormone therapies are not exactly the same. For aromatase inhibitors, the estrogen receptor can be mutated accordingly. The mutated estrogen receptor can maintain an excited conformation in the absence of estrogen, allowing it to continue to perform the receptor function to promote breast cancer cell proliferation. The resistance mechanism of breast cancer cells to the selective estrogen receptor modulator tamoxifen is complex and diverse. First, breast cancer cells can compensate for the loss of function of estrogen receptor activation functional domain-2 (AF-2) caused by tamoxifen through activating the function of estrogen receptor activation functional domain-1 (AF-1). At the same time, breast cancer cells can adjust the structure or concentration of the estrogen receptor co-activator to adapt to the conformation of the estrogen receptor bound to tamoxifen, resulting in the recovery of the function of the estrogen receptor, thereby producing drug resistance.

Selective estrogen receptor down-regulator (SERD) has shown its unique superiority in the treatment of breast cancer resistant to the above two hormone therapies. Mechanistically, selective estrogen receptor down-regulators antagonize the function of estrogen receptor, which can greatly accelerate the ubiquitination degradation of estrogen receptors in breast cancer cells (normal or mutated) and completely block estrogen/estrogen receptor signaling pathway, thereby achieving the purpose of inhibiting the growth and proliferation of normal or drug-resistant breast cancer cells. Studies have shown that selective estrogen receptor down-regulators can effectively inhibit the proliferation of hormone-resistant breast cancer cells. Fulvestrant, which is the only commercially available selective estrogen receptor down-regulator, has shown good effects in the treatment of hormone-resistant breast cancer, confirming the unique advantages of selective estrogen receptor down-regulators. However, fulvestrant itself has many problems. First, because of its poor properties, fulvestrant shows zero oral bioavailability; meanwhile, fulvestrant has a higher blood clearance. For these two reasons, this drug can only be administered by intramuscular injection. However, due to its strong lipophilic structure, fulvestrant administered by intramuscular injection also has serious problems in terms of tissue distribution. Therefore, the development of selective estrogen receptor down-regulators with oral bioavailability is an urgent medical requirement.

WO2012037411A2 reported an oral selective estrogen receptor down-regulator ARN-810, and a phase II clinical trial of this molecule in the treatment of ER-positive breast cancer is ongoing. According to reports [*J. Med. Chem.* 2015, 58 (72), 4888-4904], the important pharmacophore of the molecule is the indazole structure on the left side of the molecule, and the nitrogen atoms in the indazole structure bind to the estrogen receptor as a hydrogen bond acceptor.

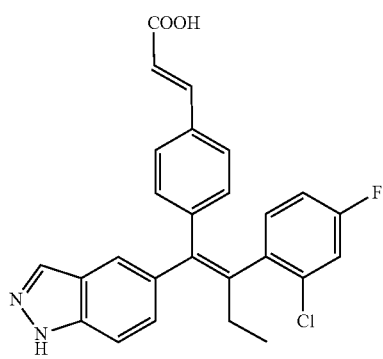

ARN-810

WO2017162206A1 reports a series of orally selective estrogen receptor down-regulation, including the preparation and biological activity of compound 1-8 (Example 8 in WO2017162206A1):

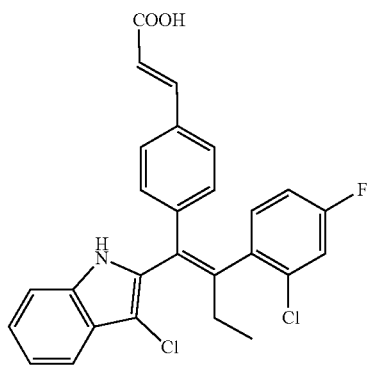

I-8

Content of the Present Invention

The present invention provides a compound of formula (I),

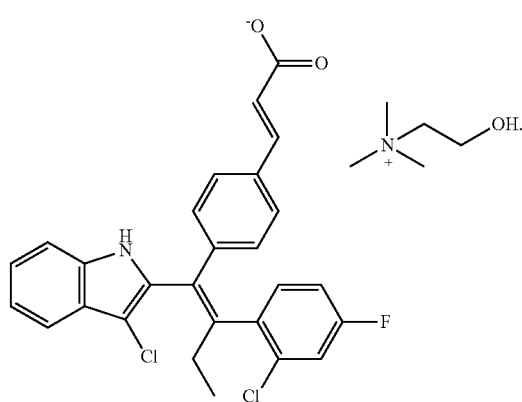

(I)

The present invention also provides a crystal form A of the compound of formula (I), wherein the X-ray powder diffraction pattern under Cu-Kα radiation has characteristic diffraction peaks at the following 2θ angles: 5.52±0.2°, 13.68±0.2°, 19.98±0.2°, 20.80±0.2°, 22.02±0.2°, 22.44±0.2°, 24.94±0.2° and 26.96±0.2°,

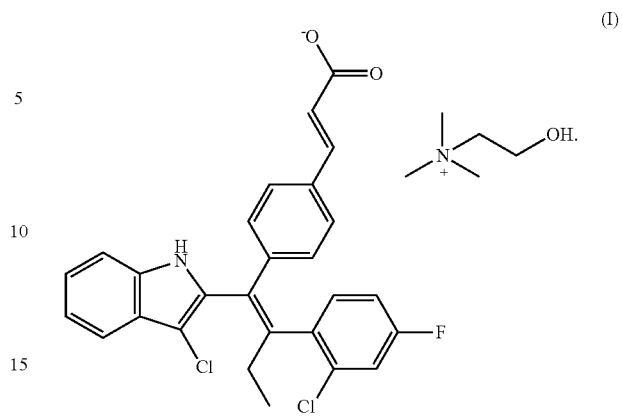

(I)

In some embodiments of the present invention, the crystal form A, has nine or more than nine, ten or more than ten, or eleven or more than eleven characteristic diffraction peaks in the X-ray powder diffraction pattern under Cu-Kα radiation at the 2θ angles selected from the group consisting of 5.52±0.2°, 13.68±0.2°, 18.86±0.2°, 19.98±0.2°, 20.80±0.2°, 21.62±0.2°, 22.02±0.2°, 22.44±0.2°, 23.34±0.2°, 24.94±0.2°, 26.96±0.2° and 28.42±0.2°.

In some embodiments of the present invention, the X-ray powder diffraction pattern of the crystal form A under Cu-Kα radiation is shown in FIG. 1.

In some embodiments of the present invention, the analysis data of the XRPD pattern of the crystal form A is shown in Table 1.

TABLE 1

Analysis data of the XRPD pattern of the crystal form A of the compound of formula (I)

| No. | 2θ Angle (°) | d-spacing (Å) | Intensity | Relative intensity (%) |
|---|---|---|---|---|
| 1 | 5.519 | 16.0002 | 891 | 84.0 |
| 2 | 10.023 | 8.8181 | 138 | 13.0 |
| 3 | 10.483 | 8.4319 | 169 | 15.9 |
| 4 | 10.962 | 8.0646 | 306 | 28.8 |
| 5 | 11.739 | 7.5328 | 259 | 24.4 |
| 6 | 12.419 | 7.1213 | 283 | 26.6 |
| 7 | 13.68 | 6.468 | 581 | 54.7 |
| 8 | 15.401 | 5.7486 | 208 | 19.6 |
| 9 | 16.239 | 5.4539 | 114 | 10.8 |
| 10 | 16.973 | 5.2196 | 165 | 15.5 |
| 11 | 17.579 | 5.041 | 113 | 10.6 |
| 12 | 18.241 | 4.8596 | 194 | 18.3 |
| 13 | 18.859 | 4.7018 | 374 | 35.2 |
| 14 | 19.181 | 4.6234 | 201 | 18.9 |
| 15 | 19.979 | 4.4405 | 573 | 54.0 |
| 16 | 20.482 | 4.3327 | 598 | 56.4 |
| 17 | 20.802 | 4.2667 | 605 | 57.0 |
| 18 | 21.618 | 4.1075 | 373 | 35.1 |
| 19 | 22.019 | 4.0335 | 655 | 61.7 |
| 20 | 22.437 | 3.9593 | 1061 | 100.0 |
| 21 | 23.341 | 3.808 | 377 | 35.5 |
| 22 | 24.939 | 3.5676 | 413 | 38.9 |
| 23 | 25.957 | 3.4298 | 156 | 14.7 |
| 24 | 26.96 | 3.3045 | 755 | 71.1 |
| 25 | 27.561 | 3.2338 | 322 | 30.3 |
| 26 | 28.038 | 3.1798 | 202 | 19.0 |
| 27 | 28.419 | 3.138 | 409 | 38.5 |
| 28 | 29.454 | 3.0301 | 63 | 5.9 |
| 29 | 29.863 | 2.9895 | 98 | 9.2 |
| 30 | 30.459 | 2.9324 | 129 | 12.2 |
| 31 | 31.062 | 2.8769 | 123 | 11.5 |
| 32 | 31.638 | 2.8258 | 47 | 4.4 |

TABLE 1-continued

Analysis data of the XRPD pattern of the crystal form A of the compound of formula (I)

| No. | 2θ Angle (°) | d-spacing (Å) | Intensity | Relative intensity (%) |
|---|---|---|---|---|
| 33 | 32.499 | 2.7528 | 186 | 17.5 |
| 34 | 33.841 | 2.6467 | 88 | 8.3 |
| 35 | 34.643 | 2.5872 | 36 | 3.4 |
| 36 | 35.035 | 2.5591 | 47 | 4.4 |
| 37 | 36.013 | 2.4918 | 42 | 3.4 |
| 38 | 37.44 | 2.4001 | 69 | 4.0 |
| 39 | 38.058 | 2.3625 | 93 | 6.5 |

In some embodiments of the present invention, the differential scanning calorimetric curve of the crystal form A has an endothermic peak at 239.46° C.±3° C.

In some embodiments of the present invention, the differential scanning calorimetric curve pattern of the crystal form A is shown in FIG. 2.

The present invention also provides a crystal form B of the compound of formula (I), wherein the X-ray powder diffraction pattern under Cu-Kα radiation has characteristic diffraction peaks at the following 2θ angles: 5.68±0.2°, 12.36±0.2°, 19.24±0.2°, 19.86±0.2°, 20.62±0.2°, 21.64±0.2°, 22.68±0.2° and 24.96±0.2°.

In some embodiments of the present invention, the crystal form B has nine or more than nine, ten or more than ten, or eleven or more than eleven characteristic diffraction peaks in the X-ray powder diffraction pattern under Cu-Kα radiation at the 2θ angle selected from the group consisting of 5.68±0.2°, 12.36±0.2°, 13.42±0.2°, 19.24±0.2°, 19.86±0.2°, 20.62±0.2°, 21.64±0.2°, 22.68±0.2°, 24.96±0.2°, 26.38±0.2°, 27.44±0.2° and 30.62±0.2°.

In some embodiments of the present invention, the X-ray powder diffraction pattern of the crystal form B under Cu-Kα radiation is shown in FIG. 3.

In some embodiments of the present invention, the analysis data of the XRPD pattern of the crystal form B is shown in Table 2.

TABLE 2

Analysis data of the XRPD pattern of the crystal form B of the compound of formula (I)

| No. | 2θ Angle (°) | d-spacing (Å) | Intensity | Relative intensity (%) |
|---|---|---|---|---|
| 1 | 5.677 | 15.5537 | 459 | 73.3 |
| 2 | 9.756 | 9.0589 | 103 | 16.5 |
| 3 | 11.315 | 7.8134 | 53 | 8.5 |
| 4 | 12.363 | 7.1538 | 352 | 56.2 |
| 5 | 13.420 | 6.5923 | 315 | 50.4 |
| 6 | 14.798 | 5.9815 | 68 | 10.9 |
| 7 | 15.406 | 5.7470 | 41 | 6.6 |
| 8 | 16.481 | 5.3744 | 62 | 9.9 |
| 9 | 17.281 | 5.1273 | 128 | 20.5 |
| 10 | 17.721 | 5.0009 | 146 | 23.3 |
| 11 | 18.898 | 4.6920 | 253 | 40.5 |
| 12 | 19.239 | 4.6096 | 432 | 68.9 |
| 13 | 19.860 | 4.4668 | 481 | 76.7 |
| 14 | 20.619 | 4.3041 | 422 | 67.3 |
| 15 | 21.641 | 4.1032 | 626 | 100.0 |
| 16 | 22.681 | 3.9173 | 390 | 62.2 |
| 17 | 23.258 | 3.8213 | 98 | 15.6 |
| 18 | 24.959 | 3.5648 | 397 | 63.4 |
| 19 | 25.240 | 3.5257 | 222 | 35.4 |
| 20 | 26.378 | 3.3760 | 278 | 44.4 |
| 21 | 27.059 | 3.2926 | 66 | 10.6 |
| 22 | 27.438 | 3.2480 | 249 | 39.8 |
| 23 | 28.098 | 3.1732 | 79 | 12.6 |
| 24 | 28.482 | 3.1313 | 93 | 14.9 |
| 25 | 29.483 | 3.0272 | 66 | 10.6 |
| 26 | 30.002 | 2.9760 | 127 | 20.3 |
| 27 | 30.622 | 2.9171 | 267 | 42.6 |
| 28 | 31.080 | 2.8752 | 219 | 34.9 |
| 29 | 33.402 | 2.6804 | 41 | 6.6 |
| 30 | 34.198 | 2.6199 | 51 | 8.1 |
| 31 | 34.985 | 2.5627 | 79 | 12.7 |
| 32 | 38.698 | 2.3249 | 49 | 7.8 |
| 33 | 39.020 | 2.3065 | 67 | 10.6 |
| / | / | / | / | / |

The present invention also provides a compound of formula (II),

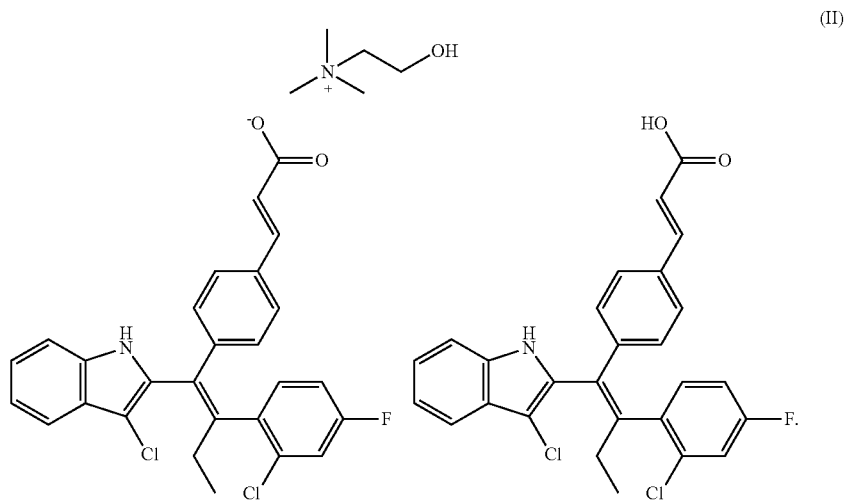

The present invention also provides a crystal form C of the compound of formula (II), wherein the X-ray powder diffraction pattern under Cu-Kα radiation is shown in FIG. 4.

In some embodiments of the present invention, the analysis data of the XRPD pattern of the crystal form C is shown in Table 3.

TABLE 3

Analysis data of the XRPD pattern of the crystal form C of the compound of formula (II)

| No. | 2θ Angle (°) | d-spacing (Å) | Intensity | Relative intensity (%) |
|---|---|---|---|---|
| 1 | 6.476 | 13.6374 | 325 | 34.6 |
| 2 | 11.021 | 8.0219 | 518 | 55.1 |
| 3 | 11.777 | 7.5081 | 100 | 10.6 |
| 4 | 12.106 | 7.3051 | 42 | 4.5 |
| 5 | 12.920 | 6.8463 | 138 | 14.7 |
| 6 | 13.997 | 6.3222 | 508 | 54.1 |
| 7 | 15.427 | 5.7389 | 92 | 9.8 |
| 8 | 15.797 | 5.6054 | 222 | 23.7 |
| 9 | 16.557 | 5.3497 | 149 | 15.9 |
| 10 | 17.282 | 5.1271 | 237 | 25.2 |
| 11 | 17.561 | 5.0460 | 285 | 30.3 |
| 12 | 18.238 | 4.8605 | 123 | 13.1 |
| 13 | 18.721 | 4.7362 | 596 | 63.4 |
| 14 | 19.579 | 4.5305 | 786 | 83.6 |
| 15 | 20.361 | 4.3581 | 586 | 62.3 |
| 16 | 21.221 | 4.1833 | 298 | 31.7 |
| 17 | 22.138 | 4.0121 | 940 | 100.0 |
| 18 | 24.018 | 3.7021 | 763 | 81.2 |
| 19 | 24.334 | 3.6547 | 190 | 20.2 |
| 20 | 24.980 | 3.5618 | 217 | 23.1 |
| 21 | 25.460 | 3.4957 | 154 | 16.4 |
| 22 | 26.022 | 3.4215 | 290 | 30.8 |
| 23 | 26.361 | 3.3782 | 465 | 49.4 |
| 24 | 27.156 | 3.2811 | 558 | 59.4 |
| 25 | 27.962 | 3.1883 | 174 | 18.5 |
| 26 | 28.222 | 3.1596 | 369 | 39.2 |
| 27 | 28.619 | 3.1166 | 244 | 26.0 |
| 28 | 30.803 | 2.9004 | 304 | 32.4 |
| 29 | 31.120 | 2.8716 | 247 | 26.3 |
| 30 | 31.759 | 2.8153 | 139 | 14.8 |
| 31 | 32.080 | 2.7878 | 132 | 14.0 |
| 32 | 33.422 | 2.6789 | 144 | 15.3 |
| 33 | 33.880 | 2.6437 | 71 | 7.6 |
| 34 | 34.858 | 2.5718 | 59 | 6.3 |
| 35 | 35.800 | 2.5062 | 53 | 5.6 |
| 36 | 36.804 | 2.4401 | 46 | 4.9 |
| 37 | 38.760 | 2.3213 | 54 | 5.7 |
| / | / | / | / | / |

The present invention also provides a compound of formula (III),

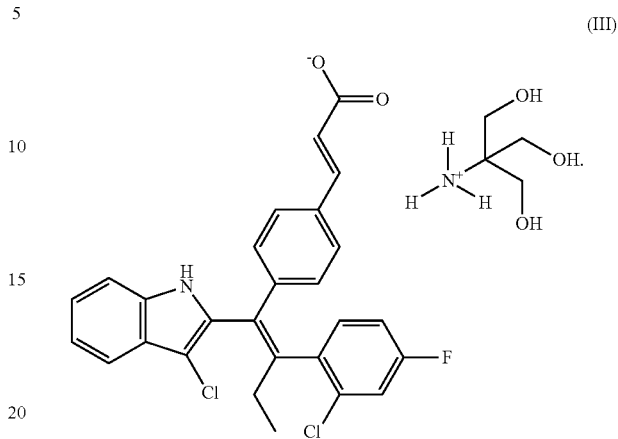

(III)

The present invention also provides a crystal form D of the compound of formula (III), wherein the X-ray powder diffraction pattern under Cu-Kα radiation is shown in FIG. 5.

In some embodiments of the present invention, the analysis data of the XRPD pattern of the crystal form D is shown in Table 4.

TABLE 4

Analysis data of the XRPD pattern of the crystal form D of the compound of formula (III)

| No. | 2θ Angle (°) | d-spacing (Å) | Intensity | Relative intensity (%) |
|---|---|---|---|---|
| 1 | 5.798 | 15.2301 | 346 | 29.5 |
| 2 | 9.7 | 9.1108 | 95 | 8.1 |
| 3 | 10.033 | 8.8092 | 235 | 20.1 |
| 4 | 11.475 | 7.705 | 142 | 12.1 |
| 5 | 12.265 | 7.2103 | 238 | 20.3 |
| 6 | 13.271 | 6.6661 | 651 | 55.5 |
| 7 | 14.433 | 6.1318 | 120 | 10.2 |
| 8 | 16.525 | 5.36 | 215 | 18.3 |
| 9 | 17.866 | 4.9607 | 167 | 14.2 |
| 10 | 18.378 | 4.8234 | 121 | 10.3 |
| 11 | 19.149 | 4.6311 | 860 | 73.4 |
| 12 | 19.901 | 4.4578 | 88 | 7.5 |
| 13 | 20.396 | 4.3505 | 1082 | 92.3 |
| 14 | 20.845 | 4.258 | 355 | 30.3 |
| 15 | 21.416 | 4.1456 | 501 | 42.7 |
| 16 | 22.797 | 3.8975 | 1172 | 100 |
| 17 | 24.021 | 3.7017 | 210 | 17.9 |
| 18 | 24.532 | 3.6257 | 239 | 20.4 |
| 19 | 25.406 | 3.503 | 123 | 10.5 |
| 20 | 26.288 | 3.3873 | 300 | 25.6 |
| 21 | 26.623 | 3.3455 | 539 | 46 |
| 22 | 27.964 | 3.188 | 344 | 29.4 |
| 23 | 28.657 | 3.1125 | 177 | 15.1 |
| 24 | 29.661 | 3.0094 | 169 | 14.4 |
| 25 | 30.69 | 2.9108 | 93 | 7.9 |
| 26 | 31.059 | 2.8771 | 63 | 5.4 |
| 27 | 31.491 | 2.8385 | 71 | 6.1 |
| 28 | 32.009 | 2.7938 | 223 | 19 |
| 29 | 33.249 | 2.6923 | 160 | 13.7 |
| 30 | 33.604 | 2.6647 | 99 | 8.4 |
| 31 | 38.144 | 2.3574 | 91 | 7.8 |
| 32 | 38.632 | 2.3287 | 58 | 4.9 |

The present invention also provides a crystal form E of the compound of formula (III), wherein the X-ray powder diffraction pattern under Cu-Kα radiation is shown in FIG. 6.

In some embodiments of the present invention, the analysis data of the XRPD pattern of the crystal form E is shown in Table 5.

TABLE 5

Analysis data of the XRPD pattern of the crystal form E of the compound of formula (III)

| No. | 2θ Angle (°) | d-spacing (Å) | Intensity | Relative intensity (%) |
|---|---|---|---|---|
| 1 | 4.896 | 18.0349 | 88 | 7.9 |
| 2 | 9.679 | 9.1306 | 69 | 6.2 |
| 3 | 10.373 | 8.5209 | 337 | 30.2 |
| 4 | 11.788 | 7.5012 | 72 | 6.5 |
| 5 | 12.54 | 7.0531 | 122 | 10.9 |
| 6 | 13.324 | 6.6395 | 84 | 7.5 |
| 7 | 14.377 | 6.1558 | 431 | 38.6 |
| 8 | 15.717 | 5.6338 | 521 | 46.7 |
| 9 | 17.22 | 5.1453 | 154 | 13.8 |
| 10 | 17.967 | 4.9329 | 76 | 6.8 |
| 11 | 19.326 | 4.5891 | 206 | 18.5 |
| 12 | 20.944 | 4.2381 | 1116 | 100 |
| 13 | 21.375 | 4.1535 | 232 | 28.9 |
| 14 | 22.602 | 3.9307 | 199 | 17.8 |
| 15 | 23.631 | 3.7619 | 112 | 10 |
| 16 | 24.04 | 3.6987 | 205 | 18.4 |
| 17 | 25.064 | 3.5499 | 195 | 17.5 |
| 18 | 26.011 | 3.4228 | 135 | 12.1 |
| 19 | 28.122 | 3.1705 | 153 | 13.7 |
| 20 | 28.458 | 3.1338 | 304 | 27.2 |
| 21 | 30.074 | 2.969 | 125 | 11.2 |
| 22 | 30.763 | 2.9041 | 70 | 6.3 |
| 23 | 31.631 | 2.8263 | 145 | 13 |
| 24 | 33.189 | 2.6971 | 90 | 8.1 |

The present invention also provides a compound of formula (IV),

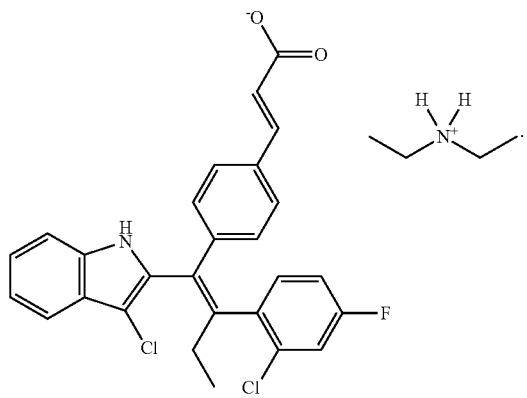

(IV)

The present invention also provides a crystal form F of the compound of formula (IV), wherein the X-ray powder diffraction pattern under Cu-Kα radiation is shown in FIG. 7.

In some embodiments of the present invention, the analysis data of the XRPD pattern of the crystal form F is shown in Table 6.

TABLE 6

Analysis data of the XRPD pattern of the crystal form F of the compound of formula (IV)

| No. | 2θ Angle (°) | d-spacing (Å) | Intensity | Relative intensity (%) |
|---|---|---|---|---|
| 1 | 5.102 | 17.3079 | 350 | 39.2 |
| 2 | 6.9 | 12.8008 | 368 | 41.3 |
| 3 | 7.785 | 11.3466 | 892 | 100 |
| 4 | 10.827 | 8.165 | 376 | 42.2 |
| 5 | 11.359 | 7.7833 | 68 | 7.6 |
| 6 | 11.869 | 7.45 | 345 | 38.7 |
| 7 | 12.461 | 7.0973 | 73 | 8.2 |
| 8 | 13.23 | 6.6868 | 241 | 27 |
| 9 | 13.606 | 6.5026 | 587 | 65.8 |
| 10 | 14.078 | 6.2855 | 710 | 79.6 |
| 11 | 14.866 | 5.9543 | 84 | 9.4 |
| 12 | 16.664 | 5.3156 | 227 | 25.4 |
| 13 | 17.393 | 5.0944 | 114 | 12.8 |
| 14 | 18.04 | 4.9132 | 158 | 17.7 |
| 15 | 19.287 | 4.5983 | 236 | 26.5 |
| 16 | 19.801 | 4.48 | 434 | 48.7 |
| 17 | 20.41 | 4.3477 | 269 | 30.2 |
| 18 | 21.017 | 4.2234 | 146 | 16.4 |
| 19 | 22.305 | 3.9825 | 172 | 19.3 |
| 20 | 22.852 | 3.8883 | 343 | 38.5 |
| 21 | 24.095 | 3.6904 | 178 | 20 |
| 22 | 24.888 | 3.5746 | 138 | 15.5 |
| 23 | 25.243 | 3.5251 | 229 | 25.7 |
| 24 | 26.227 | 3.395 | 221 | 24.8 |
| 25 | 26.821 | 3.3213 | 108 | 12.1 |
| 26 | 27.334 | 3.26 | 198 | 22.2 |
| 27 | 28.931 | 3.0836 | 97 | 10.9 |
| 28 | 29.297 | 3.046 | 72 | 8.1 |
| 29 | 30.841 | 2.8968 | 67 | 7.5 |
| 30 | 34.874 | 2.5705 | 71 | 8 |

The present invention also provides a crystal form G of the compound of formula (IV), wherein the X-ray powder diffraction pattern under Cu-Kα radiation is shown in FIG. 8.

In some embodiments of the present invention, the analysis data of the XRPD pattern of the crystal form G is shown in Table 7.

TABLE 7

Analysis data of the XRPD pattern of the crystal form G of the compound of formula (IV)

| No. | 2θ Angle (°) | d-spacing (Å) | Intensity | Relative intensity (%) |
|---|---|---|---|---|
| 1 | 4.57 | 19.3182 | 195 | 44.5 |
| 2 | 6.021 | 14.6669 | 161 | 36.8 |
| 3 | 6.962 | 12.6869 | 438 | 100 |
| 4 | 7.33 | 12.0502 | 172 | 39.3 |
| 5 | 11.055 | 7.9966 | 141 | 32.2 |
| 6 | 12.207 | 7.2446 | 272 | 62.1 |
| 7 | 12.719 | 6.9543 | 369 | 84.2 |
| 8 | 16.863 | 5.2533 | 101 | 23.1 |
| 9 | 17.955 | 4.9363 | 74 | 16.9 |
| 10 | 18.93 | 4.6841 | 156 | 35.6 |
| 11 | 19.324 | 4.5894 | 75 | 17.1 |
| 12 | 19.901 | 4.4576 | 105 | 24 |
| 13 | 21.079 | 4.2112 | 152 | 34.7 |
| 14 | 22.301 | 3.983 | 142 | 32.4 |
| 15 | 24.792 | 3.5883 | 157 | 35.8 |
| 16 | 25.913 | 3.4355 | 95 | 21.7 |
| 17 | 26.386 | 3.375 | 96 | 21.9 |
| 18 | 26.861 | 3.3164 | 69 | 15.8 |

TABLE 7-continued

Analysis data of the XRPD pattern of the crystal form G of the compound of formula (IV)

| No. | 2θ Angle (°) | d-spacing (Å) | Intensity | Relative intensity (%) |
|---|---|---|---|---|
| 19 | 28.811 | 3.0962 | 72 | 16.4 |
| 20 | 29.684 | 3.0071 | 73 | 16.7 |
| 21 | 31.477 | 2.8398 | 76 | 17.4 |
| 22 | 33.411 | 2.6797 | 59 | 13.5 |

The present invention also provides a compound of formula (V),

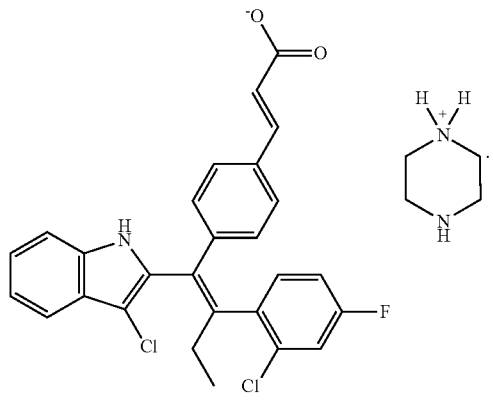

(IV)

The present invention also provides a crystal form H of the compound of formula (V), wherein the X-ray powder diffraction pattern under Cu-Kα radiation is shown in FIG. 9.

In some embodiments of the present invention, the analysis data of the XRPD pattern of the crystal form H is shown in Table 8.

TABLE 8

Analysis data of the XRPD pattern of the crystal form H of the compound of formula (V)

| No. | 2θ Angle (°) | d-spacing (Å) | Intensity | Relative intensity (%) |
|---|---|---|---|---|
| 1 | 6.566 | 13.4503 | 197 | 31.3 |
| 2 | 7.69 | 11.4875 | 167 | 26.5 |
| 3 | 10.478 | 8.4359 | 66 | 10.5 |
| 4 | 11.961 | 7.3932 | 80 | 12.7 |
| 5 | 12.599 | 7.02 | 248 | 39.4 |
| 6 | 15.224 | 5.8149 | 491 | 77.9 |
| 7 | 16.369 | 5.4108 | 152 | 24.1 |
| 8 | 16.879 | 5.2484 | 119 | 18.9 |
| 9 | 17.551 | 5.0489 | 630 | 100 |
| 10 | 18.557 | 4.7775 | 126 | 20 |
| 11 | 19.837 | 4.472 | 106 | 16.8 |
| 12 | 20.686 | 4.2904 | 283 | 44.9 |
| 13 | 21.494 | 4.1307 | 206 | 32.7 |
| 14 | 22.836 | 3.8911 | 435 | 69 |
| 15 | 23.744 | 3.7441 | 278 | 44.1 |
| 16 | 25.105 | 3.5442 | 229 | 36.3 |
| 17 | 26.643 | 3.343 | 230 | 36.5 |
| 18 | 28.536 | 3.1254 | 293 | 46.5 |

TABLE 8-continued

Analysis data of the XRPD pattern of the crystal form H of the compound of formula (V)

| No. | 2θ Angle (°) | d-spacing (Å) | Intensity | Relative intensity (%) |
|---|---|---|---|---|
| 19 | 29.643 | 3.0112 | 69 | 11 |
| 20 | 30.824 | 2.8984 | 151 | 24 |
| 21 | 32.6 | 2.7444 | 56 | 8.9 |
| 22 | 34.099 | 2.6272 | 69 | 11 |

The present invention also provides a crystal form I of the compound of formula (V), wherein the X-ray powder diffraction pattern under Cu-Kα radiation is shown in FIG. 10.

In some embodiments of the present invention, the analysis data of the XRPD pattern of the crystal form H is shown in Table 9.

TABLE 9

Analysis data of the XRPD pattern of the crystal form I of the compound of formula (V)

| No. | 2θ Angle (°) | d-spacing (Å) | Intensity | Relative intensity (%) |
|---|---|---|---|---|
| 1 | 5.157 | 17.1214 | 110 | 26.3 |
| 2 | 8.102 | 10.903 | 221 | 52.9 |
| 3 | 11.155 | 7.9256 | 108 | 25.8 |
| 4 | 11.807 | 7.4894 | 176 | 42.1 |
| 5 | 12.205 | 7.2456 | 84 | 20.1 |
| 6 | 12.789 | 6.916 | 62 | 14.8 |
| 7 | 14.492 | 6.1071 | 243 | 58.1 |
| 8 | 14.945 | 5.923 | 171 | 40.9 |
| 9 | 17.651 | 5.0205 | 418 | 100 |
| 10 | 18.813 | 4.7129 | 237 | 56.7 |
| 11 | 19.939 | 4.4493 | 213 | 51 |
| 12 | 20.529 | 4.3228 | 298 | 71.3 |
| 13 | 20.823 | 4.2623 | 151 | 36.1 |
| 14 | 21.83 | 4.068 | 77 | 18.4 |
| 15 | 23.073 | 3.8516 | 417 | 99.8 |
| 16 | 23.744 | 3.7442 | 78 | 18.7 |
| 17 | 24.533 | 3.6255 | 147 | 35.2 |
| 18 | 25.816 | 3.4481 | 158 | 37.8 |
| 19 | 26.265 | 3.3902 | 119 | 28.5 |
| 20 | 27.687 | 3.2192 | 224 | 53.6 |

The present invention also provides a crystal form J of the compound of formula (V), wherein the X-ray powder diffraction pattern under Cu-Kα radiation is shown in FIG. 11.

In some embodiments of the present invention, the analysis data of the XRPD pattern of the crystal form J is shown in Table 10.

TABLE 10

Analysis data of the XRPD pattern of the crystal form J of the compound of formula (V)

| No. | 2θ Angle (°) | d-spacing (Å) | Intensity | Relative intensity (%) |
|---|---|---|---|---|
| 1 | 5.03 | 17.5537 | 118 | 41.3 |
| 2 | 7.569 | 11.671 | 199 | 69.6 |
| 3 | 8.005 | 11.0357 | 125 | 43.7 |
| 4 | 11.638 | 7.5975 | 183 | 64 |
| 5 | 13.073 | 6.7665 | 286 | 100 |
| 6 | 13.547 | 6.531 | 137 | 47.9 |
| 7 | 14.375 | 6.1566 | 106 | 37.1 |
| 8 | 14.869 | 5.9532 | 129 | 45.1 |
| 9 | 16.464 | 5.3796 | 102 | 35.7 |

TABLE 10-continued

Analysis data of the XRPD pattern of the crystal form J of the compound of formula (V)

| No. | 2θ Angle (°) | d-spacing (Å) | Intensity | Relative intensity (%) |
|---|---|---|---|---|
| 10 | 17.825 | 4.9719 | 204 | 71.3 |
| 11 | 19.127 | 4.6362 | 181 | 63.3 |
| 12 | 19.602 | 4.525 | 216 | 75.5 |
| 13 | 20.431 | 4.3432 | 209 | 73.1 |
| 14 | 21.688 | 4.0942 | 73 | 25.5 |
| 15 | 21.986 | 4.0395 | 96 | 33.6 |
| 16 | 22.444 | 3.958 | 111 | 38.8 |
| 17 | 22.894 | 3.8813 | 146 | 51 |
| 18 | 24.832 | 3.5826 | 76 | 26.6 |
| 19 | 25.522 | 3.4873 | 115 | 40.2 |
| 20 | 25.939 | 3.4322 | 120 | 42 |
| 21 | 27.509 | 3.2397 | 88 | 30.8 |
| / | / | / | / | / |

The present invention also provides a compound of formula (VI),

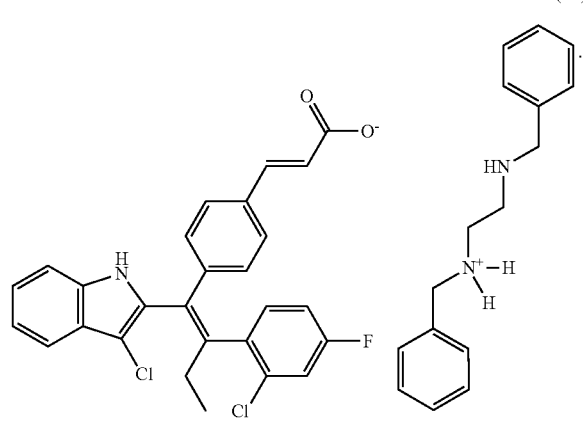

(VI)

The present invention also provides a crystal form K of the compound of formula (VI), wherein the X-ray powder diffraction pattern under Cu-Kα radiation is shown in FIG. 12.

In some embodiments of the present invention, the analysis data of the XRPD pattern of the crystal form K is shown in Table 11.

TABLE 11

Analysis data of the XRPD pattern of the crystal form K of the compound of formula (VI)

| No. | 2θ Angle (°) | d-spacing (Å) | Intensity | Relative intensity (%) |
|---|---|---|---|---|
| 1 | 5.935 | 14.8801 | 194 | 19.9 |
| 2 | 6.763 | 13.0593 | 126 | 12.9 |
| 3 | 11.219 | 7.8806 | 609 | 62.3 |
| 4 | 12.009 | 7.3638 | 196 | 20.1 |
| 5 | 13.035 | 6.7864 | 218 | 22.3 |
| 6 | 13.564 | 6.5229 | 92 | 9.4 |
| 7 | 14.627 | 6.0511 | 162 | 16.6 |
| 8 | 15.164 | 5.8378 | 371 | 38 |
| 9 | 16.031 | 5.524 | 977 | 100 |
| 10 | 16.621 | 5.3292 | 244 | 25 |
| 11 | 17.451 | 5.0777 | 433 | 44.3 |
| 12 | 17.807 | 4.977 | 551 | 56.4 |

TABLE 11-continued

Analysis data of the XRPD pattern of the crystal form K of the compound of formula (VI)

| No. | 2θ Angle (°) | d-spacing (Å) | Intensity | Relative intensity (%) |
|---|---|---|---|---|
| 13 | 18.671 | 4.7484 | 846 | 86.6 |
| 14 | 20.132 | 4.4071 | 666 | 68.2 |
| 15 | 21.039 | 4.2191 | 267 | 27.3 |
| 16 | 22.403 | 3.9652 | 382 | 39.1 |
| 17 | 22.975 | 3.8677 | 616 | 63.1 |
| 18 | 23.288 | 3.8164 | 570 | 58.3 |
| 19 | 23.922 | 3.7168 | 536 | 54.9 |
| 20 | 24.965 | 3.5637 | 703 | 72 |
| 21 | 26.128 | 3.4077 | 226 | 23.1 |
| 22 | 27.705 | 3.2172 | 366 | 37.5 |
| 23 | 28.355 | 3.1449 | 128 | 13.1 |
| 24 | 29.145 | 3.0614 | 374 | 38.3 |
| 25 | 29.8 | 2.9956 | 109 | 11.2 |
| 26 | 30.482 | 2.9301 | 87 | 8.9 |
| 27 | 30.941 | 2.8877 | 72 | 7.4 |
| 28 | 32.223 | 2.7757 | 90 | 9.2 |
| 29 | 33.584 | 2.6663 | 103 | 10.5 |
| 30 | 36.224 | 2.4778 | 57 | 5.8 |
| 31 | 38.159 | 2.3565 | 57 | 5.8 |
| 32 | 38.91 | 2.3127 | 69 | 7.1 |

The present invention also provides uses of the compounds or the crystal forms mentioned above in manufacturing a medicament for treating the breast cancer.

Technical Effects

Compared with the free acid form of the compound 1-8 reported in WO2017162206A1, the solubility of the compound of formula (I) of the present invention and the crystal form thereof in water is nearly hundredfold improved; in the solubility test of biological media, the solubility of the compound of formula (I) and the crystal form thereof has also been significantly improved; in in vivo pharmacokinetic studies, the compound of formula (I) and the crystal form thereof exhibited superior properties, and the amount of exposure in the organism was significantly increased. These good properties of the compound of formula (I) and the crystal form thereof make it more conducive to the preparation of medicines, benefit patients, and meet clinical needs.

Definitions and Explanations

Unless otherwise indicated, the following terms and phrases used herein are intended to have the following meanings. A particular term or phrase should not be considered uncertain or unclear without a special definition, but should be understood according to its ordinary meaning. When a trade name appears herein, it is intended to refer to its corresponding product or its active ingredient.

The intermediate compounds of the present invention can be prepared by a variety of synthetic methods well known to those skilled in the art, including the following specific embodiments, the embodiments formed by combining them with other chemical synthesis methods, and equivalent alternatives well known to those skilled in the art, preferred embodiments include, but are not limited to, the embodiments of the present invention.

The chemical reactions of the specific embodiments of the present invention are performed in suitable solvents, and the solvents must be suitable for the chemical changes of the present invention and the reagents and materials required for the same. In order to obtain the compounds of the present invention, it is sometimes necessary for those skilled in the art to modify or select the synthetic steps or reaction schemes based on the existing embodiments.

The present invention will be described in detail below through embodiments, which do not imply any limitation to the present invention.

All solvents used in the present invention are commercially available and can be used without further purification.

The present invention uses the following abbreviations: MW stands for microwave; r.t. stands for room temperature; aq stands for aqueous solution; DCM stands for dichloromethane; THF stands for tetrahydrofuran; DMSO stands for dimethyl sulfoxide; NMP stands for N-methylpyrrolidone; EtOAc stands for ethyl acetate; EtOH stands for ethanol; MeOH stands for methanol; dioxane stands for dioxane; HOAc stands for acetic acid; Boc stands for tert-butoxycarbonyl, Cbz stands for benzyloxycarbonyl, both of Boc and Cbz are amine protecting groups; $Boc_2O$ stands for di-tert-butyl dicarbonate; DIPEA stands for ethyldiisopropylamine; TEA or $Et_3N$ stands for triethylamine; $BnNH_2$ stands for benzylamine; $PMBNH_2$ stands for p-methoxybenzylamine; KOAc stands for potassium acetate; NaOAc stands for sodium acetate; $Cs_2CO_3$ stands for cesium carbonate; $K_2CO_3$ stands for potassium carbonate; $NaHCO_3$ stands for sodium bicarbonate; $Na_2SO_4$ stands for sodium sulfate; pyridine stands for pyridine; NaOH stands for sodium hydroxide; TEA or $Et_3N$ stands for triethylamine; NaH stands for sodium hydrogen; LiHMDS stands for lithium bis(trimethylsilyl)amide; i-PrMgBr stands for isopropylmagnesium bromide; t-BuOK stands for potassium t-butoxide; t-BuONa stands for sodium t-butoxide; $Pd_2(dba)_3$ stands for tris(dibenzylideneacetone)dipalladium; $Pd(PPh_3)_4$ stands for tetrakis(triphenylphosphine)palladium; $Pd(dppf)Cl_2CH_2Cl_2$ stands for 1,1'-bis(diphenylphosphino)ferrocene-palladium(II)dichloride dichloromethane complex; $Pd(OAc)_2$ stands for palladium acetate; $Pd(PPh_3)_2Cl_2$ stands for palladium bis(triphenylphosphine)dichloride; $Pd(PPh_3)_3Cl$ stands for stands for rhodium tris(triphenylphosphine)chloride; $Pd(OH)_2$ stands for palladium hydroxide; Xantphos stands for 4,5-bis(diphenylphosphino)-9,9-dimethylxanthene; Xphos stands for 2-(dicyclohexylphosphino)-2',4',6'-tri-iso-propyl-1,1'-biphenyl; BINAP stands for (±)-2,2'-bis(diphenylphosphino)-1,1'-binaphthyl; Xantphos stands for 4,5-bis(diphenylphosphino)-9,9-dimethylxanthene; Xphos-Pd-G1 stands for chloro(2-dicyclohexylphosphino-2',4',6'-triisopropyl-1,1'-biphenyl)[2-(2'-aminoethyl) phenyl]palladium(II); Xphos-PD-$G_2$ stands for chloro(2-dicyclohexylphosphino-2',4',6'-triisopropyl-1,1'-biphenyl)[2-(2'-amino-1,1'-b iphenyl)]palladium(II); Xphos-Pd-G3 stands for methanesulfonato(2-dicyclohexylphosphino-2',4',6'-tri-iso-propyl-1,1'-biphenyl)(2'-amino-1,1'-biphenyl-2-yl)palladium(II); $I_2$ stands for iodine; LiCl stands for lithium chloride; HCl stands for hydrochloric acid; maleic acid stands for maleic acid.

Compounds are named by hand or Chemdraw® software, and commercially available compounds use the supplier catalog names thereof.

X-Ray Powder Diffractometer (XRPD) Method
   Instrument model: Bruker D8 advance X-ray diffractometer.
   Test method: about 10-20 mg sample was used for XRPD detection.
   X-ray Tube: Cu, Kα, (λ=1.54056 Å).
   X-ray tube voltage: 40 kV, X-ray tube current: 40 mA.
   Divergence slit: 0.60 mm.
   Detector slit: 10.50 mm.
   Anti-scattering slit: 7.10 mm.
   Scanning range: 3-40 deg or 4-40 deg.
   Step diameter: 0.02 deg.
   Step length: 0.12 seconds.
   Rotation speed of sample tray: 15 rpm.

Differential Scanning Calorimeter (DSC) Method
   Instrument model: TA Q2000 differential scanning calorimeter.
   Test method: samples (about 1 mg) were sealed in DSC aluminum pans for testing, and heated at a heating rate of 10° C./min from room temperature to 250° C. (or 280° C.), at a flow rate of 50 mL/min N2.

Thermal Gravimetric Analyzer (TGA) Method
   Instrument model: TA Q5000 thermal gravimetric analyzer.
   Test method: samples (2 to 5 mg) were disposed in TGA platinum pans for testing. The samples were heated from room temperature to 300° C. or 20% weight loss at 25 mL/min N2 with a heating rate of 10° C./min.

DETAILED DESCRIPTION OF THE EMBODIMENT

Figure 1:
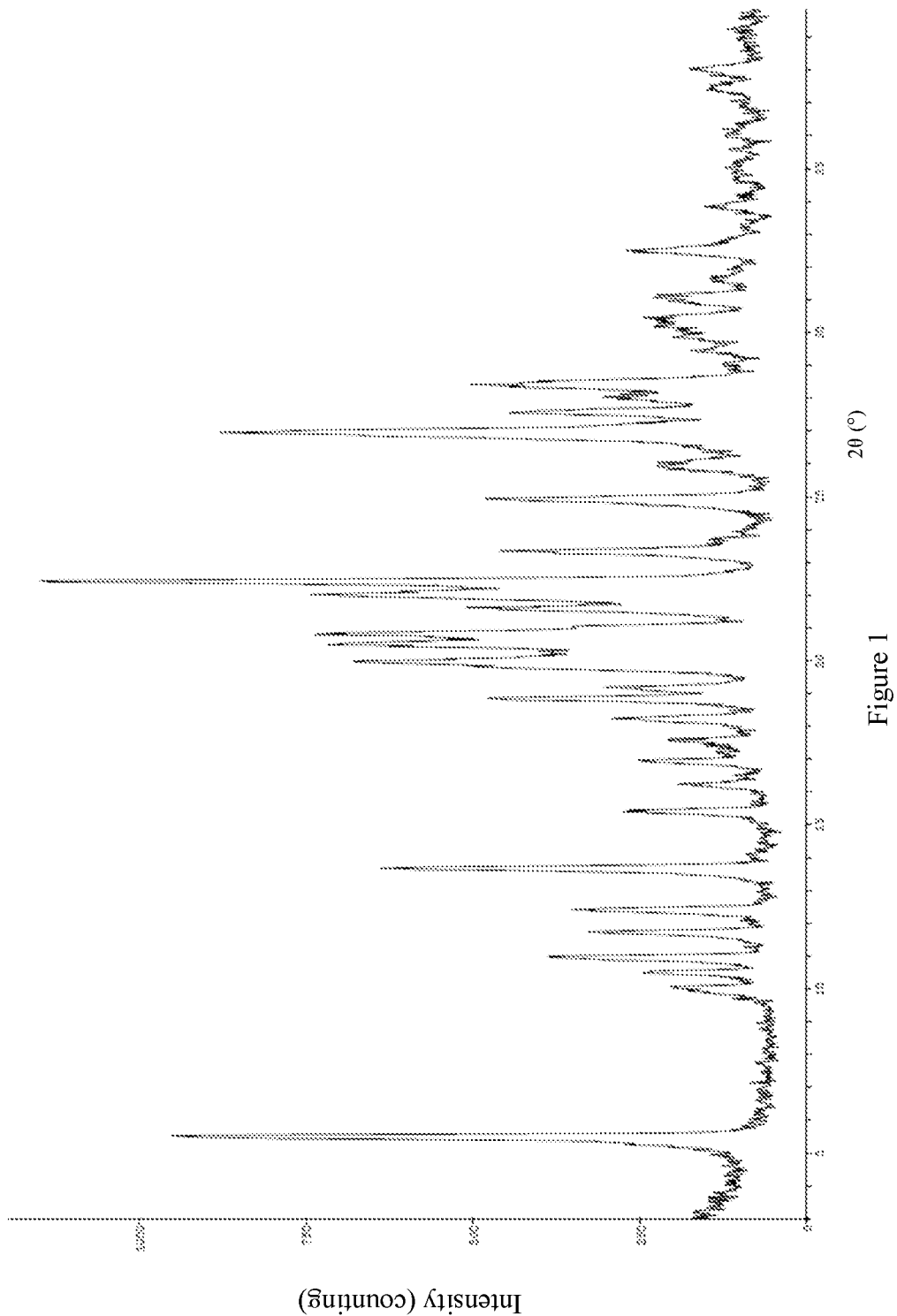
FIG. 1 is an XRPD pattern of the crystal form A of the compound of formula (I).
Figure 2:
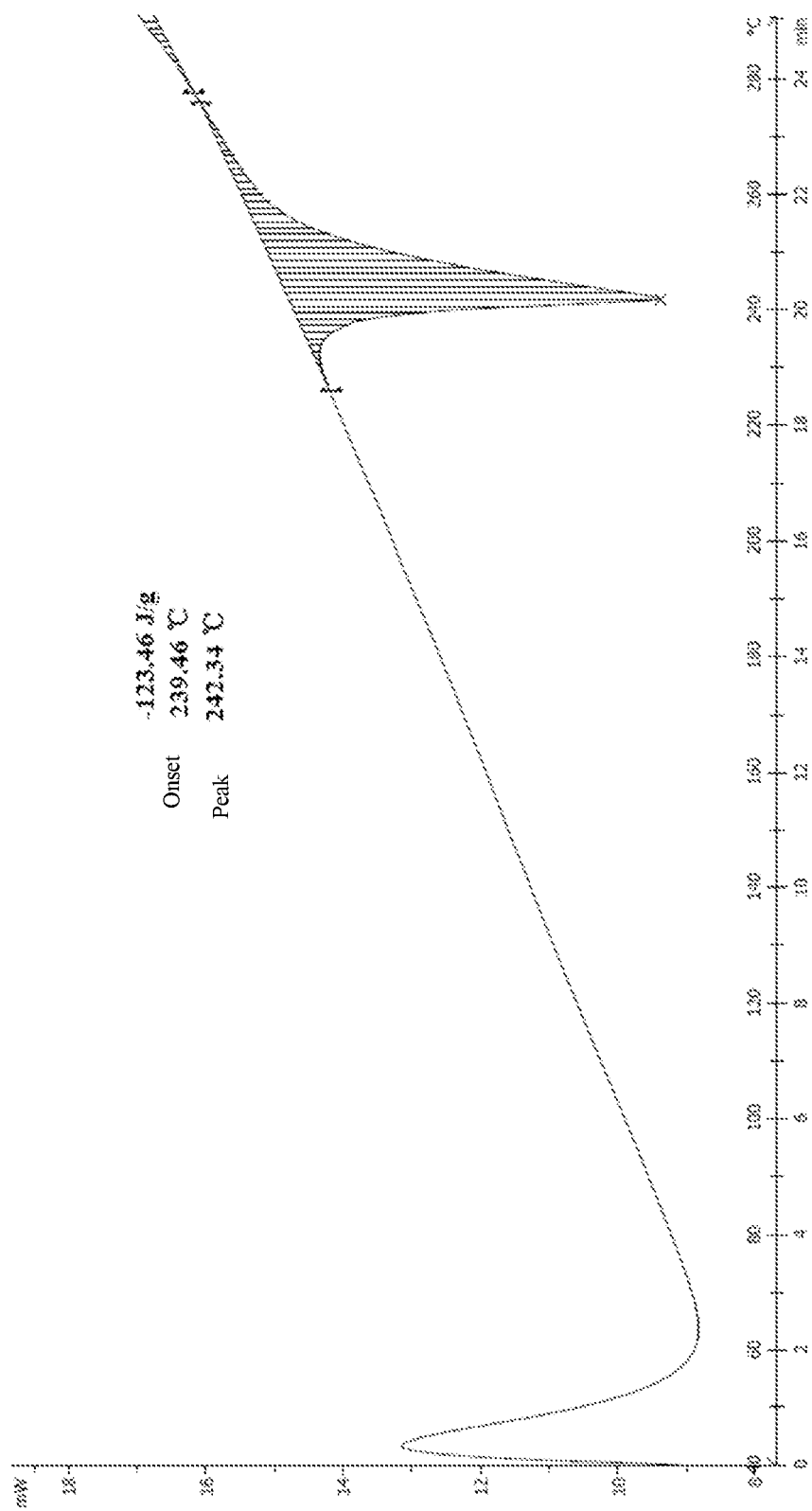
FIG. 2 is a DSC pattern of the crystal form A of the compound of formula (I).
Figure 3:
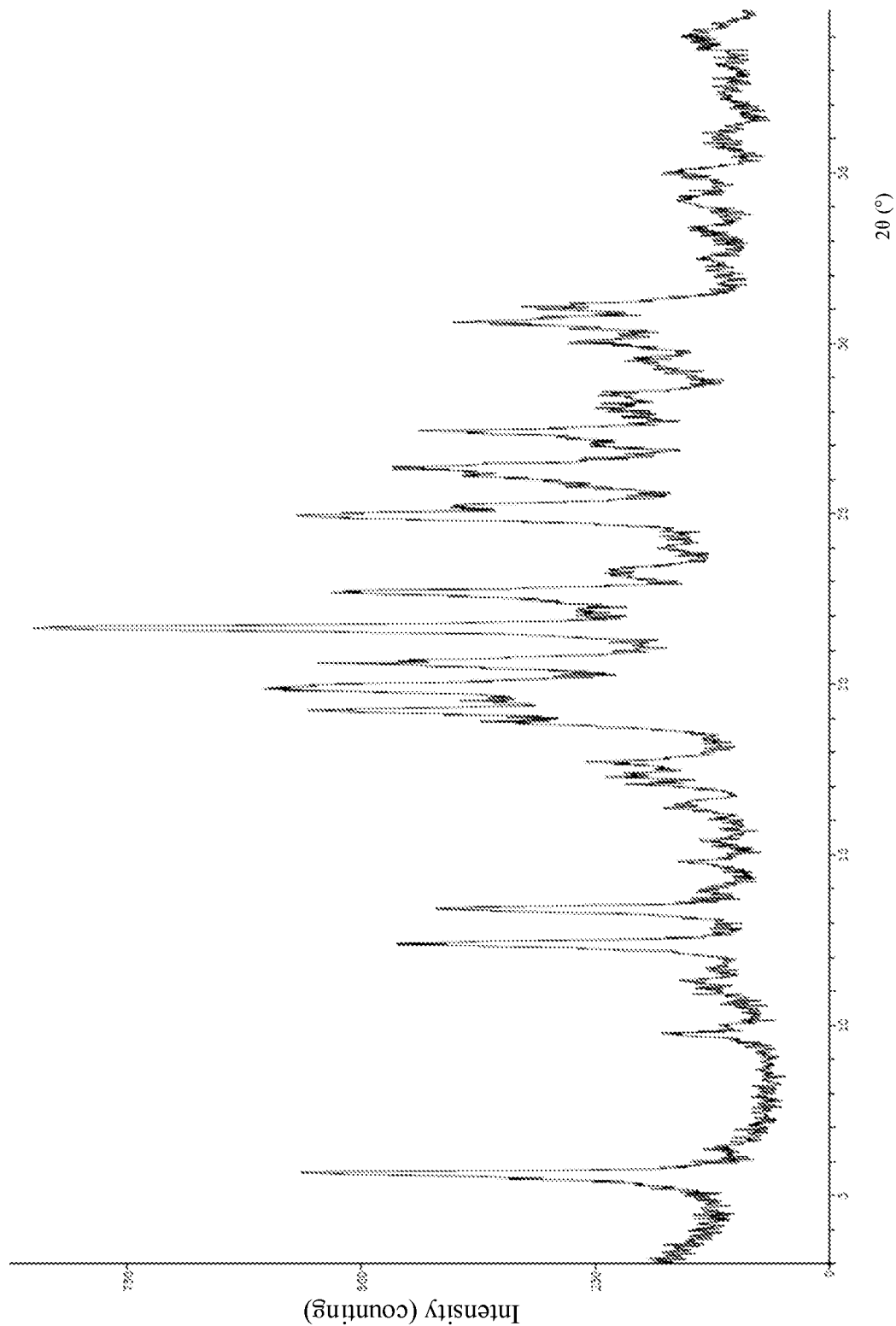
FIG. 3 is an XRPD pattern of the crystal form B of the compound of formula (I).
Figure 4:
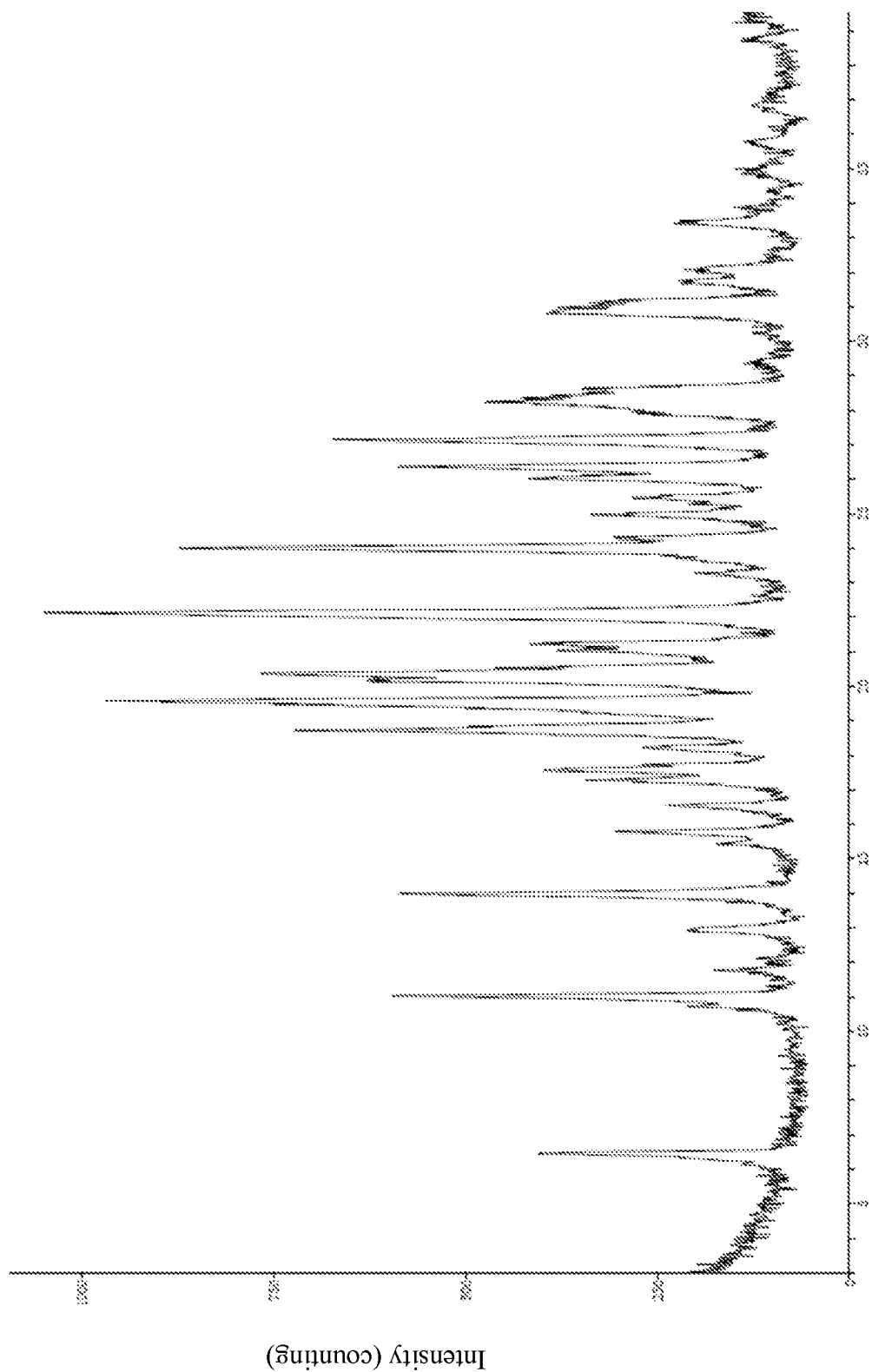
FIG. 4 is an XRPD pattern of the crystal form C of the compound of formula (II).
Figure 5:
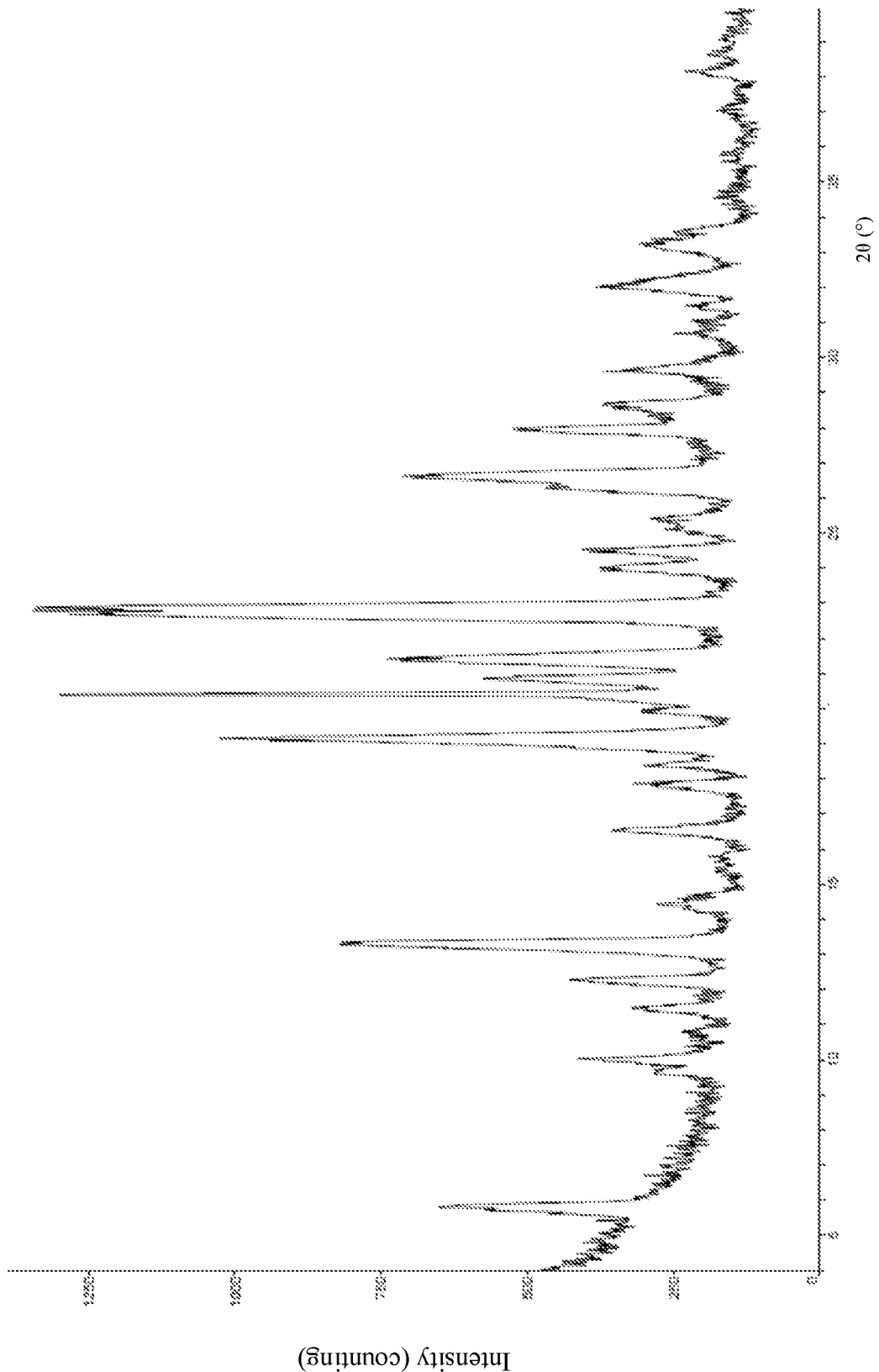
FIG. 5 is an XRPD pattern of the crystal form D of the compound of formula (III).
Figure 6:
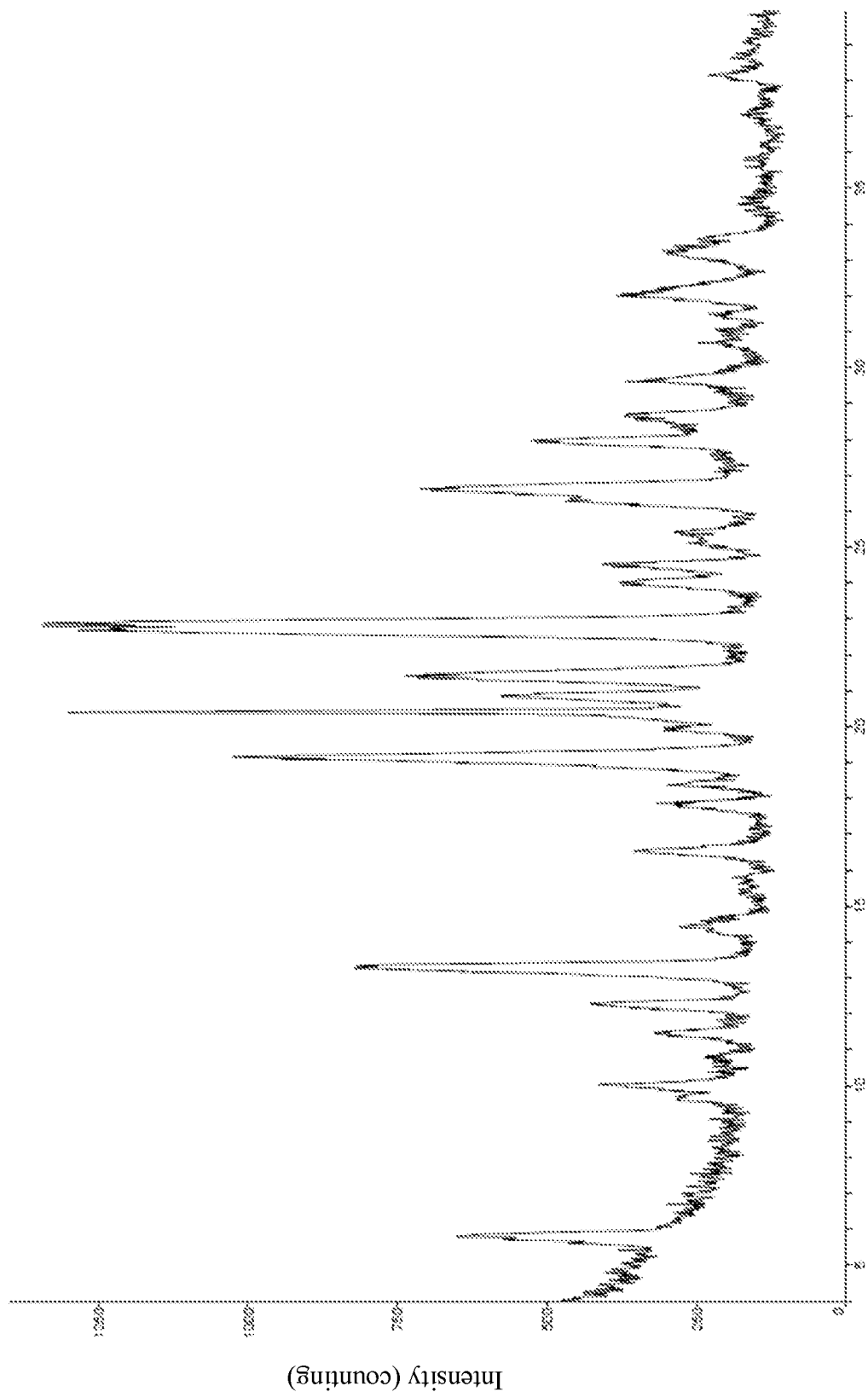
FIG. 6 is an XRPD pattern of the crystal form E of the compound of formula (III).
Figure 7:
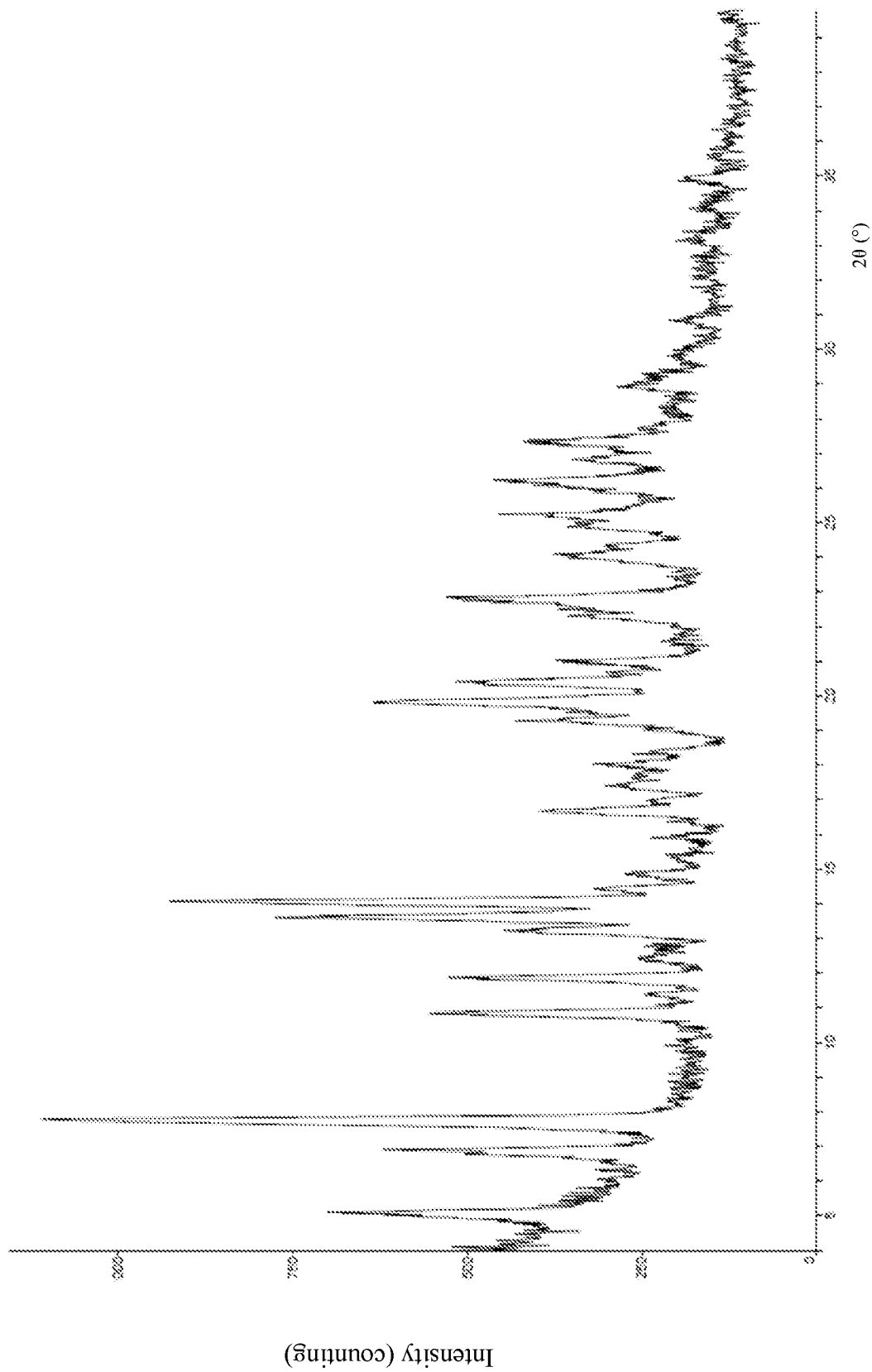
FIG. 7 is an XRPD pattern of the crystal form F of the compound of formula (IV).
Figure 8:
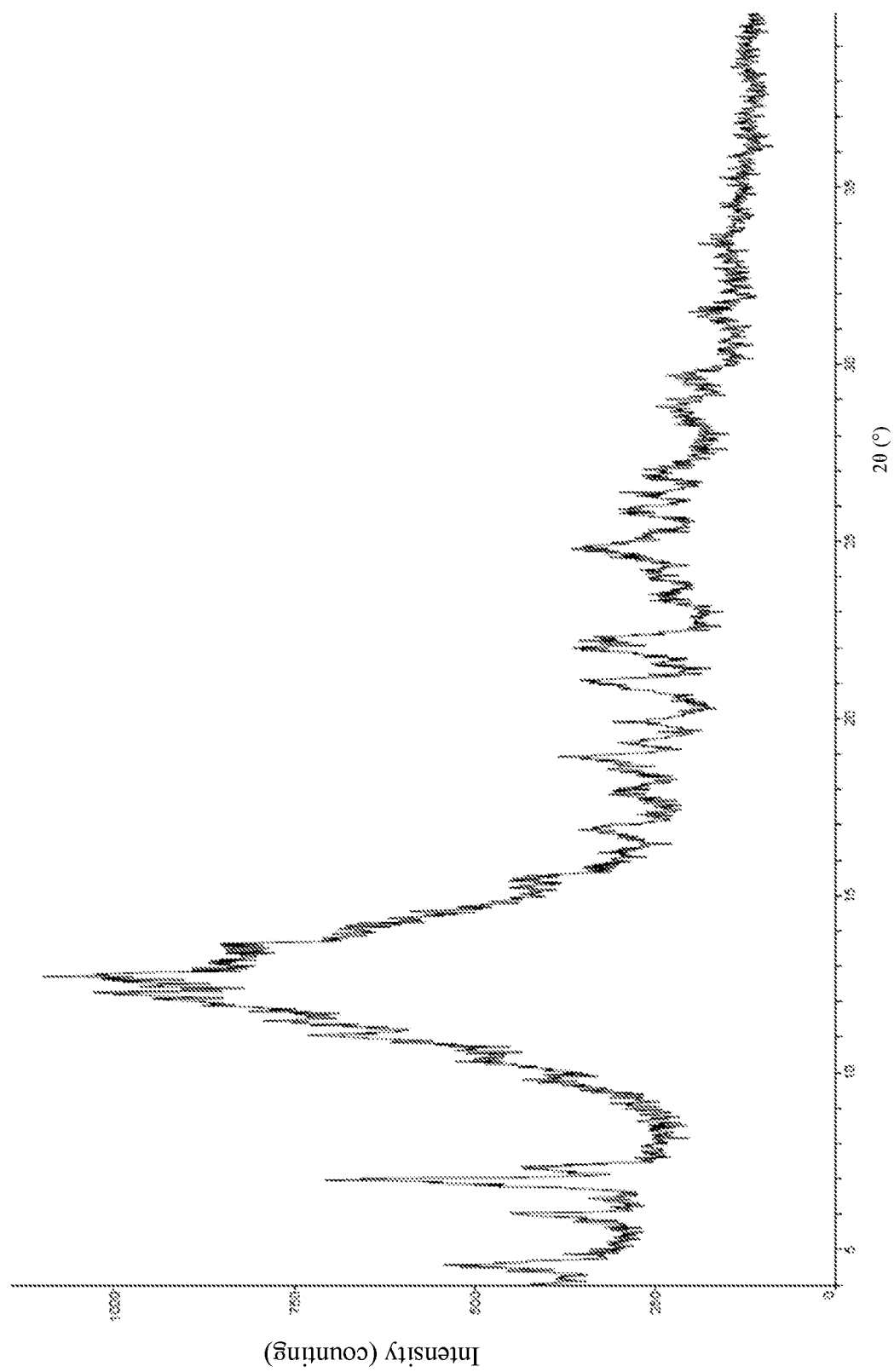
FIG. 8 is an XRPD pattern of the crystal form G of the compound of formula (IV).
Figure 9:
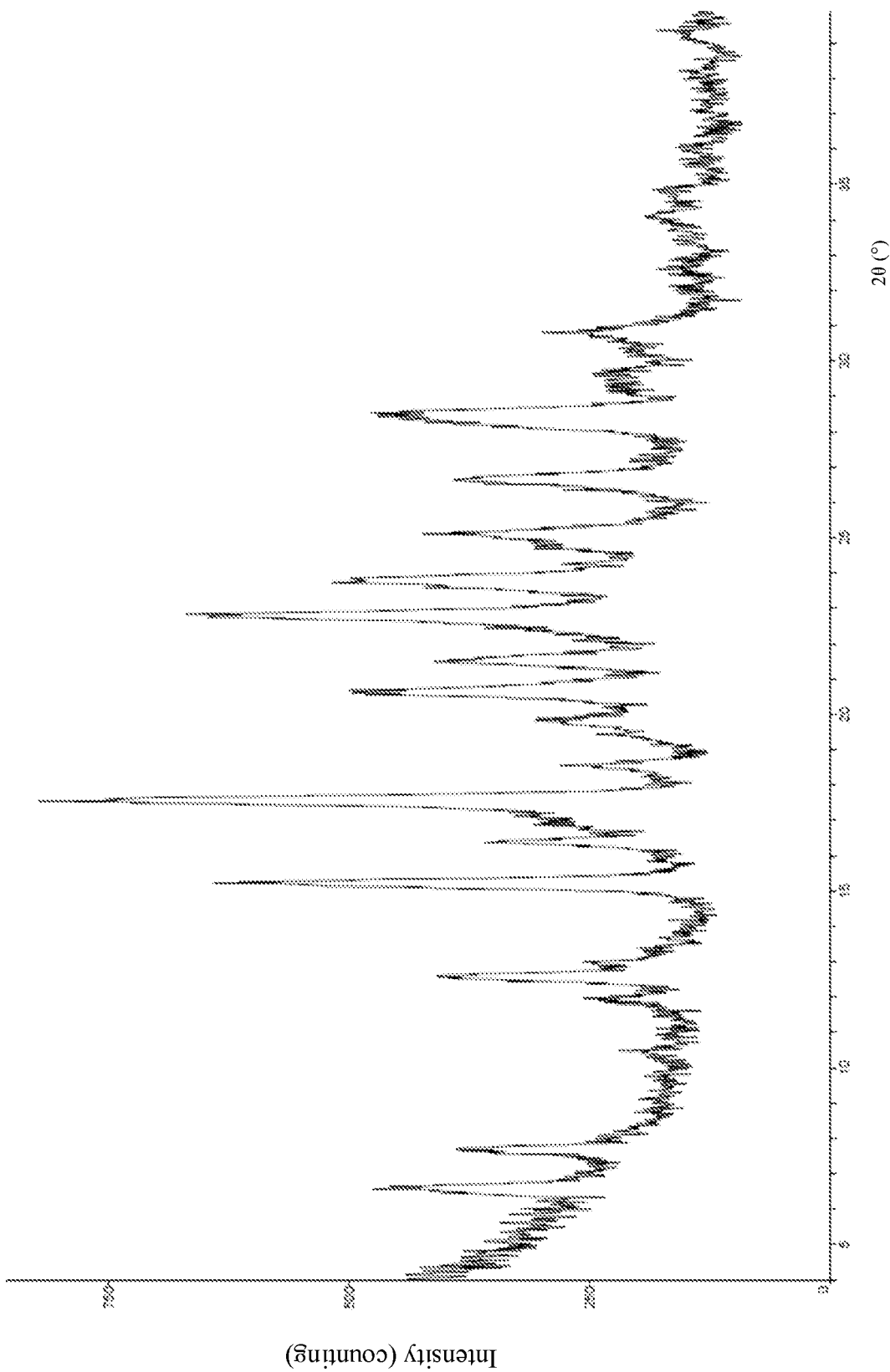
FIG. 9 is an XRPD pattern of the crystal form H of the compound of formula (V).
Figure 10:
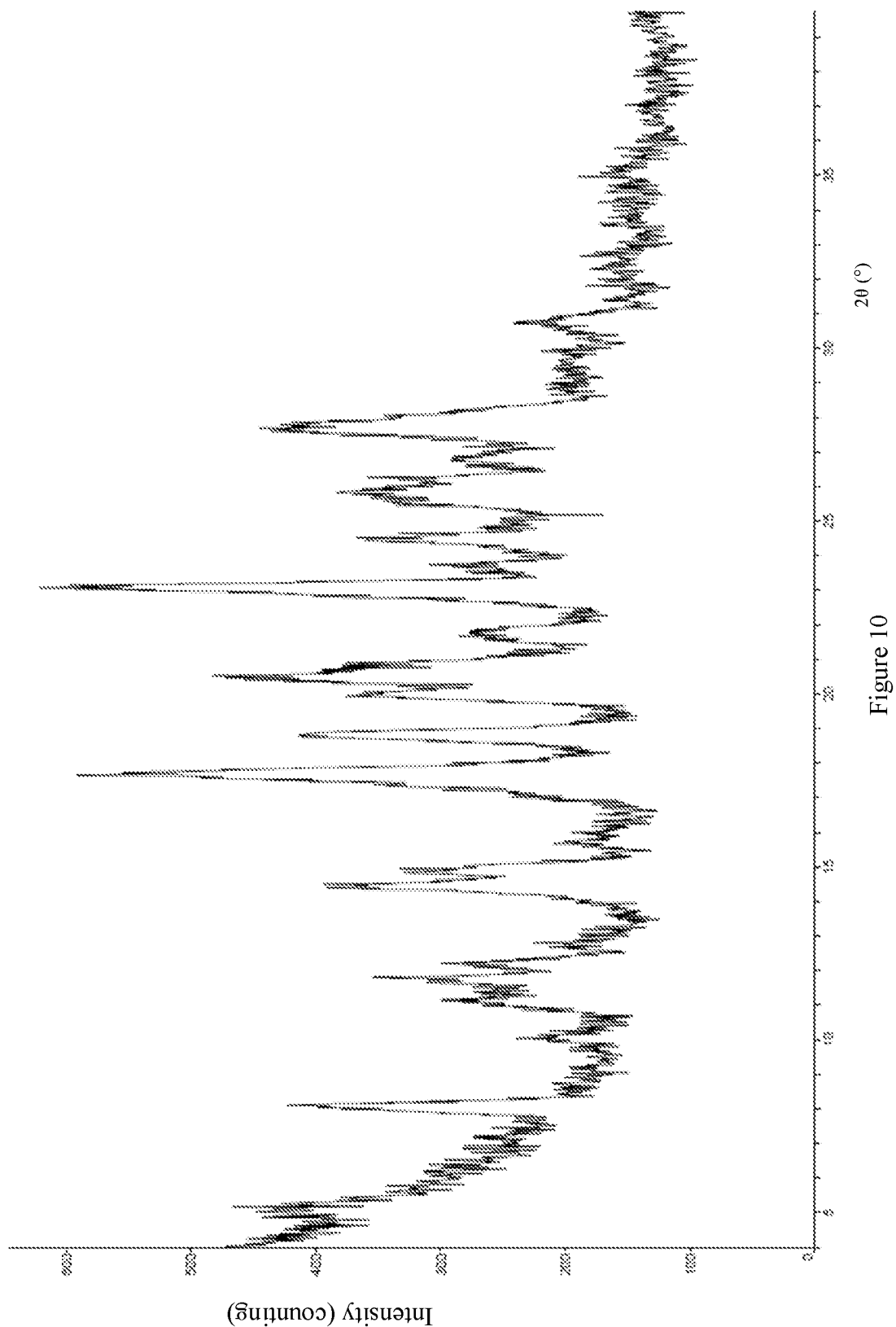
FIG. 10 is an XRPD pattern of the crystal form I of the compound of formula (V).
Figure 11:
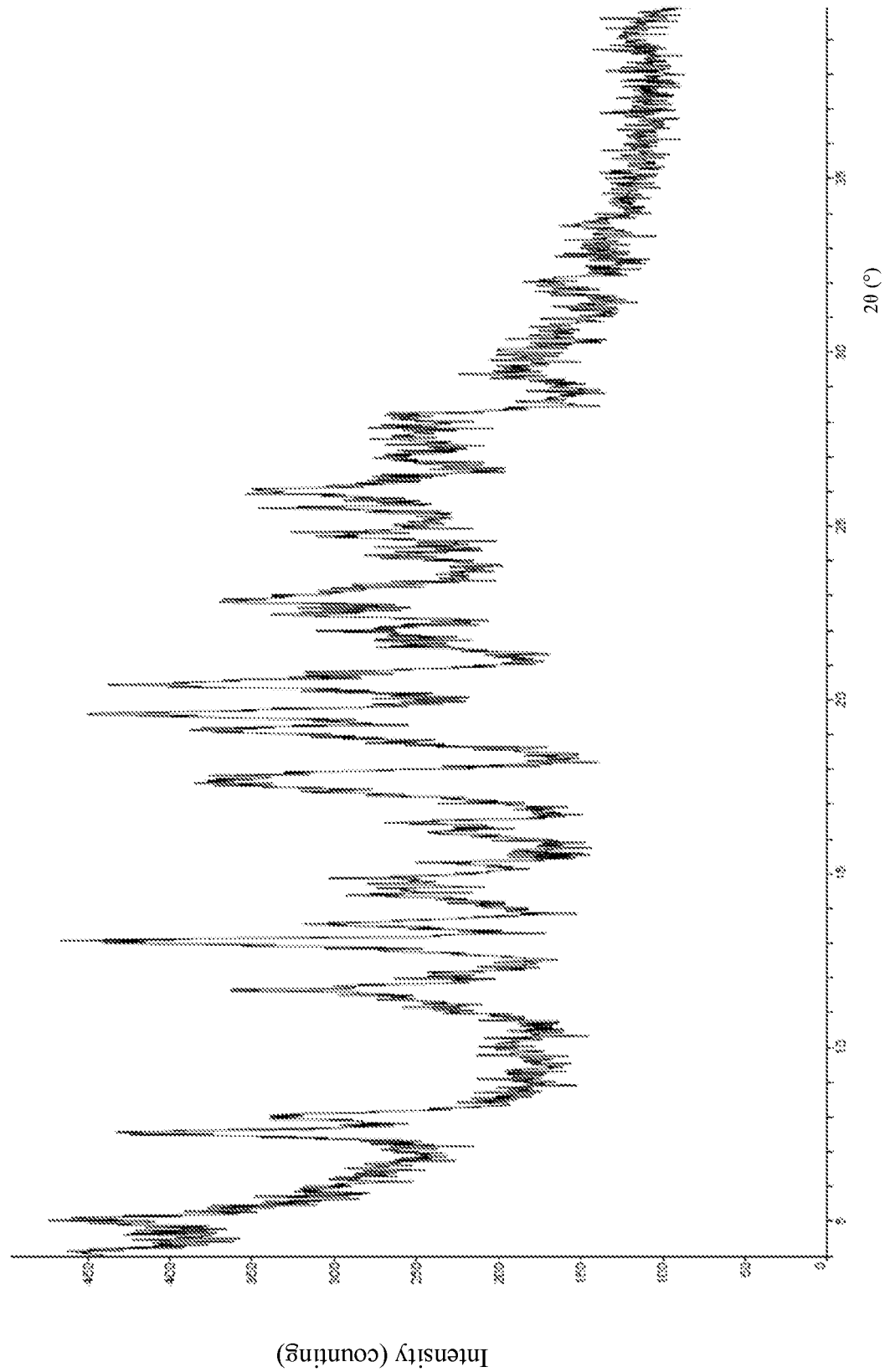
FIG. 11 is an XRPD pattern of the crystal form J of the compound of formula (V).
Figure 12:
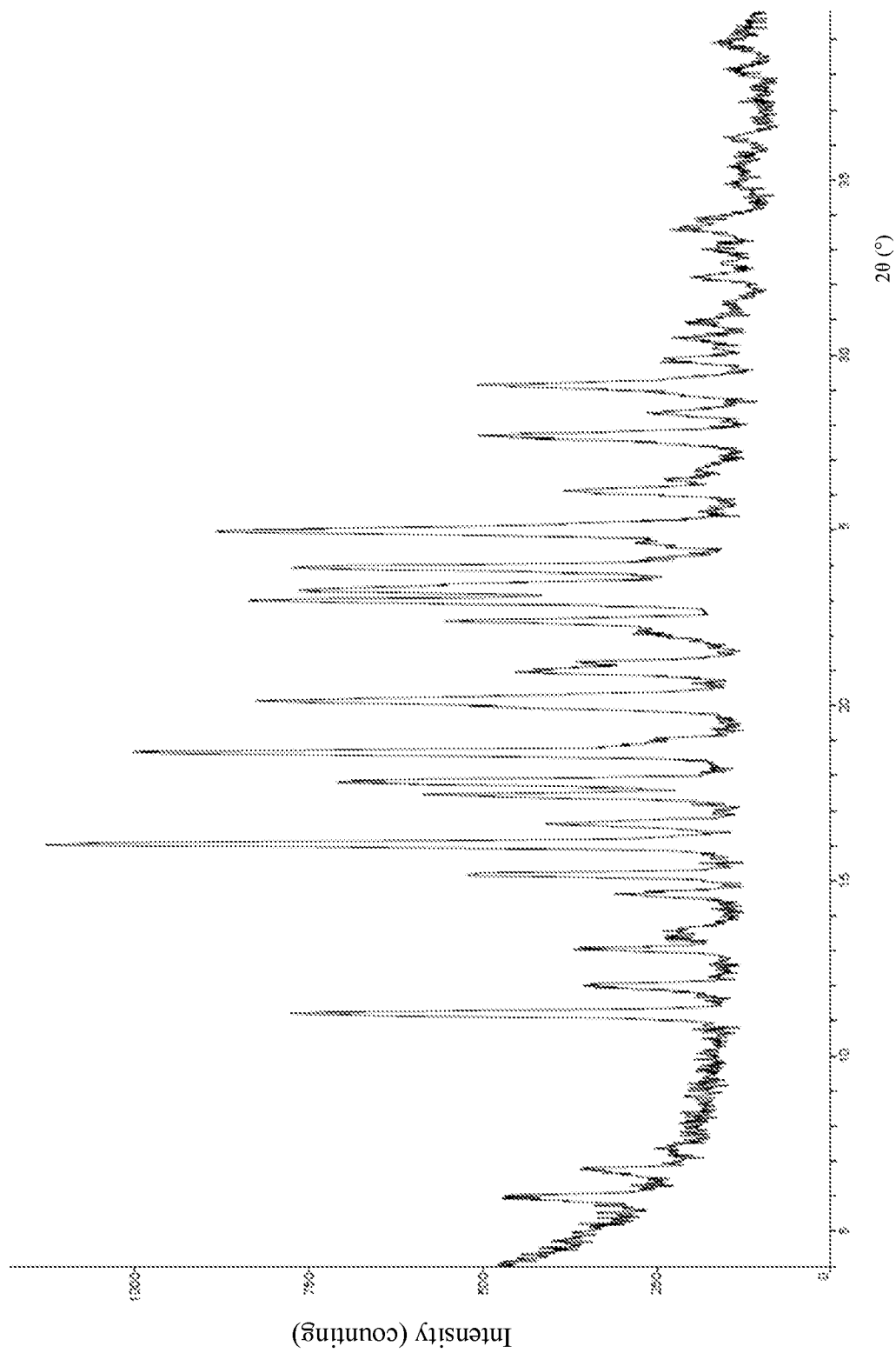
FIG. 12 is an XRPD pattern of the crystal form K of the compound of formula (VI).

In order to better understand the content of the present invention, the following Embodiments further illustrate the present invention, but the present invention is not limited.

Embodiment 1: Preparation for the Crystal Form A of the Compound of Formula (I)

Anhydrous methanol (4.9 L), choline aqueous solution (49.5% by weight, 467.60 g), and anhydrous methanol (0.12 L) were added to the reaction kettle successively and the temperature was adjusted to 25° C. Then a solution of compound 1-8 (1004.15 g) in anhydrous methanol (4.90 L) was added dropwise to the reaction kettle, and the temperature was controlled between 20-25° C. After the addition, the mixture was stirred at around 35° C. for 5 h before the termination of the heating and stirring. Ethyl acetate (10.04 L) was added to the reaction solution, followed by concentrating to constant weight at 40° C., and the process was repeated twice. Ethyl acetate (16.58 L) was added again, the mixture was heated to 79° C. and refluxed for 42 hours, then the stirring stopped after the mixture was cooled down to room temperature. The mixture was filtered, and the filter cake was washed with ethyl acetate (3.00 L), collected and dried at ambient temperature (15-25° C.) for 19 h. The filter cake was dried at 45-50° C. and −0.8 MPa for about 28 h to obtain the crystal form A of the compound of formula (I).

1H NMR (400 MHz, DMSO-d6) δ=12.14 (br s, 1H), 7.53-7.45 (m, 1H), 7.45-7.41 (m, 1H), 7.41-7.33 (m, 1H), 7.31-7.22 (m, 1H), 7.22-7.08 (m, 5H), 7.02-6.89 (m, 3H), 6.25 (d, J=16.0 Hz, 1H), 3.94-3.77 (m, 2H), 3.47-3.41 (m, 2H), 3.13 (s, 9H), 2.49-2.31 (m, 2H), 0.88 (t, J=7.6 Hz, 3H)

Embodiment 2: Preparation for the Crystal Form B of the Compound of Formula (I)

At 20° C., hydroxycholine methanol solution (45% by weight, 1 g) was added to compound 1-8 (1 g) and ethyl acetate (10 mL) and the mixture was stirred at 20° C. for 16 hours to obtain a yellow solution, which became a yellow suspension due to gradual precipitation. The mixture was filtered and the filter cake was washed with ethyl acetate (5 mL×3) to obtain the crystal form B of the compound of formula (I) by drying in vacuum.

1H NMR (400 MHz, DMSO-d6) δ=11.88 (br s, 1H), 7.47 (d, J=8.4 Hz, 1H), 7.41 (d, J=8.4 Hz, 2H), 7.28 (d, J=8.4 Hz, 1H), 7.20-7.08 (m, 5H), 6.98-6.90 (m, 3H), 6.26 (d, J=16.0 Hz, 1H), 3.88-3.80 (m, 2H), 3.45-3.38 (m, 2H), 3.11 (s, 9H), 2.47-2.35 (m, 2H), 0.87 (t, J=7.2 Hz, 3H)

Embodiment 3: Preparation for the Crystal Form C of the Compound of Formula (II)

1 g Compound 1-8 was dissolved in 10 mL ethyl acetate and the mixture was stirred at 50° C. for 30 min, hydroxycholine aqueous solution (50% by weight, 248.86 mg) was added at 50° C. and the mixture was stirred at 50° C. for 5 h, then cooled to 20° C. and stirred for 12 h. Solids were precipitated, then filtered off, and the filter cake was washed with ethyl acetate (3 mL×3) and concentrated to give 1.08 g white solid of the crystal form C of the compound of formula (II).

1H NMR (400 MHz, DMSO-d6) δ=11.62 (br s, 1H), 7.49 (d, J=8.4 Hz, 1H), 7.41 (d, J=8.4 Hz, 2H), 7.32-7.25 (m, 3H), 7.20-7.08 (m, 4H), 6.97 (d, J=8.4 Hz, 2H), 6.38 (d, J=16.0 Hz, 1H), 3.88-3.82 (m, 1H), 3.43-3.38 (m, 1H), 3.11 (s, 4.5H), 2.50-2.32 (m, 2H), 0.89 (t, J=7.6 Hz, 3H)

Embodiment 4: Preparation for the Crystal of the Compound of Formula (III)

1) Preparation for the Crystal Form D of the Compound of Formula (III)

0.2 g Free acid was dissolved in acetonitrile (2 mL) and the mixture was stirred at 50° C. for 30 minutes, 55.48 mg trometamol was added and the mixture was stirred at 50° C. for 5 hours, then cooled to 25° C. and stirred for 16 hours. Solids were precipitated, and then filtered off, the filter cake was washed with n-heptane (5 mL), and the solid was concentrated to obtain 145 mg bright yellow solid.

1H NMR (400 MHz, DMSO-d6) δ=11.52 (br s, 1H), 7.49 (d, J=8.0 Hz, 1H), 7.40 (d, J=8.0 Hz, 2H), 7.32-7.23 (m, 3H), 7.22-7.10 (m, 4H), 6.97 (d, J=8.0 Hz, 2H), 6.32 (d, J=15.6 Hz, 1H), 3.41 (s, 6H), 2.48-2.39 (m, 2H), 0.87 (t, J=7.6 Hz, 3H)

2) Preparation for the Crystal Form E of the Compound of Formula (III)

0.2 g Free acid was dissolved in isopropanol (2 mL) and the mixture was stirred at 50° C. for 30 minutes. 55.48 mg Tristearin was added and the mixture was stirred at 50° C. for 5 hours, then cooled to 25° C. and stirred for 16 hours. The solution was kept clear and poured into a glass vial containing 20 mL n-heptane, then the mixture was filtered to obtain a viscous oil, and concentrated to obtain 103 mg bright yellow solid.

1H NMR (400 MHz, DMSO-d6) δ=11.50 (br s, 1H), 7.48 (d, J=8.0 Hz, 1H), 7.40 (d, J=8.0 Hz, 2H), 7.33-7.22 (m, 3H), 7.21-7.08 (m, 4H), 6.96 (d, J=8.0 Hz, 2H), 6.31 (d, J=16.0 Hz, 1H), 3.38 (s, 6H), 2.50-2.39 (m, 2H), 0.88 (t, J=7.6 Hz, 3H)

Embodiment 5: Preparation for the Compound of Formula (IV)

1) Preparation for the Crystal Form F of the Compound of Formula (IV)

0.2 g Free acid was dissolved in acetone (2 mL) and the mixture was stirred at 50° C. for 30 mins, 33.50 mg diethylamine was added and the mixture was stirred at 50° C. for 5 h, then cooled to 25° C. and stirred for 16 h. A large amount of white solid was precipitated, filtered off, and the filter cake was washed with acetone (2 mL×3), and the filter cake was concentrated to obtain 161 mg white solid.

1H NMR (400 MHz, DMSO-d6) δ=11.56 (br s, 1H), 7.51 (d, J=7.2 Hz, 1H), 7.40 (d, J=7.6 Hz, 2H), 7.31-7.28 (m, 3H), 7.20-7.10 (m, 4H), 6.96 (d, J=8.4 Hz, 2H), 6.32 (d, J=16.0 Hz, 1H), 2.76 (d, J=7.2 Hz, 4H), 2.51-2.43 (m, 2H), 1.11 (d, J=7.2 Hz, 6H), 0.89 (t, J=7.6 Hz, 3H)

2) Preparation for the Crystal Form G of the Compound of Formula (IV)

0.2 g Free acid was dissolved in isopropanol (2 mL) and the mixture was stirred at 50° C. for 30 mins, 33.50 mg diethylamine was added and the mixture was stirred at 50° C. for 5 h, then cooled to 25° C. and stirred for 16 h. A large amount of white solid was precipitated, filtered off, and the filter cake was washed with acetone (2 mL×3), and the filter cake was concentrated to obtain 163 mg white solid.

1H NMR (400 MHz, DMSO-d6) δ=11.56 (br s, 1H), 7.51 (d, J=7.2 Hz, 1H), 7.40 (d, J=7.6 Hz, 2H), 7.31-7.28 (m, 3H), 7.20-7.10 (m, 4H), 6.97 (d, J=8.0 Hz, 2H), 6.33 (d, J=16.0 Hz, 1H), 2.76 (d, J=7.2 Hz, 4H), 2.51-2.43 (m, 2H), 1.11 (d, J=7.2 Hz, 6H), 0.89 (t, J=7.6 Hz, 3H)

Embodiment 6: Preparation for the Crystal of the Compound of Formula (V)

1) Preparation for the Crystal Form H of the Compound of Formula (V)

0.2 g Free acid was dissolved in acetone (2 mL) and the mixture was stirred at 50° C. for 30 mins, 39.45 mg piperazine was added and the mixture was stirred at 50° C. for 5 h, then cooled to 25° C. and stirred for 16 h. A large amount of white solid was precipitated, filtered off, and the filter cake was washed with acetone (2 mL×3), and the filter cake was concentrated to obtain white solids.

1H NMR (400 MHz, DMSO-d6) δ=11.55 (br s, 1H), 7.49 (d, J=8.0 Hz, 1H), 7.43-7.37 (m, 2H), 7.31-7.29 (m, 3H), 7.19-7.11 (m, 4H), 6.96 (d, J=8.4 Hz, 2H), 6.32 (d, J=15.6 Hz, 1H), 2.78 (s, 8H), 2.50-2.41 (m, 2H), 0.89 (t, J=7.6 Hz, 3H)

2) Preparation for the Crystal Form I of the Compound of Formula (V)

0.2 g Free acid was dissolved in acetonitrile (2 mL) and the mixture was stirred at 50° C. for 30 mins, 39.45 mg piperazine was added and the mixture was stirred at 50° C. for 5 h, then cooled to 25° C. and stirred for 16 h. A large amount of white solid was precipitated, filtered off, and the filter cake was washed with acetone (2 mL×3), and the filter cake was concentrated to obtain white solids.

1H NMR (400 MHz, DMSO-d6) δ=11.55 (br s, 1H), 7.49 (d, J=8.0 Hz, 1H), 7.43-7.37 (m, 2H), 7.31-7.29 (m, 3H), 7.19-7.12 (m, 4H), 6.96 (d, J=8.0 Hz, 2H), 6.32 (d, J=16.0 Hz, 1H), 2.78 (s, 8H), 2.50-2.41 (m, 2H), 0.89 (t, J=7.6 Hz, 3H)

3) Preparation for the Crystal Form J of the Compound of Formula (V)

0.2 g Free acid was dissolved in isopropanol (2 mL) and the mixture was stirred at 50° C. for 30 mins, 39.45 mg piperazine was added and the mixture was stirred at 50° C. for 5 h, then cooled to 25° C. and stirred for 16 h. A large amount of white solid was precipitated, filtered off, and the filter cake was washed with acetone (2 mL×3), and the filter cake was concentrated to obtain white solids.

1H NMR (400 MHz, DMSO-d6) δ=11.54 (br s, 1H), 7.50 (d, J=8.0 Hz, 1H), 7.43-7.37 (m, 2H), 7.33-7.25 (m, 3H), 7.21-7.14 (m, 4H), 6.96 (d, J=8.4 Hz, 2H), 6.33 (d, J=16.0 Hz, 1H), 2.76 (s, 8H), 2.50-2.35 (m, 2H), 0.89 (t, J=7.6 Hz, 3H)

Embodiment 7: Preparation for the Crystal Form K of the Compound of Formula (VI)

0.2 g Free acid was dissolved in acetonitrile (2 mL) and the mixture was stirred at 50° C. for 30 mins, 110.08 mg benzathine was added and the mixture was stirred at 50° C. for 5 h, then cooled to 25° C. and stirred for 16 h. A large amount of white solid was precipitated, filtered off, and the filter cake was washed with acetonitrile (2 mL×3), and the filter cake was concentrated to obtain white solids.

1H NMR (400 MHz, DMSO-d6) δ=11.53 (br s, 1H), 7.51 (d, J=7.2 Hz, 1H), 7.45-7.05 (m, 19H), 7.01-6.98 (m, 2H), 6.39 (d, J=16.0 Hz, 1H), 3.73 (s, 4H), 2.66 (s, 4H), 2.50-2.42 (m, 2H), 0.91-0.89 (m, 3H)

Embodiment 8: Solubility Test

Assay materials: compound 1-8, crystal form A of the compound of the formula (I), water, FaSSIF (simulated pre-meal intestinal fluid), FeSSIF (simulated post-meal intestinal fluid).

Assay method: compound 1-8 and the crystal form A of the compound of formula (I) were weighed in four portions and added to a 4 mL glass vial respectively, then 2 mL biological vehicle (FaSSIF, FeSSIF) and purified water were added respectively, the mixtures were mixed uniformly and the magnets were added to the suspensions, the mixtures were placed on a magnetic stirring heater for stirring (at 37° C., protected from light). Samples were taken after 24 h, and the sample solution was quickly centrifuged, and the supernatant was diluted suitable folds and its concentration was determined by HPLC.

Assay results: see Table 12.

TABLE 12

Solubility Comparison-solubility of different biological vehicle

| Compounds to be tested | Biological vehicle | | |
|---|---|---|---|
| | $H_2O$ (mg/mL)* | FaSSIF (mg/mL)* | FeSSIF (mg/mL)* |
| compound I-8 | 0.008 | 0.117 | 0.440 |
| Crystal Form A of the compound of formula (I) | 0.870 | 1.650 | 3.590 |

*the solubility of the crystal form A of the compound of formula (I) was calculated based on the free acid.

Experiment conclusion: compared with compound 1-8, the solubility of the crystal form A of the compound of formula (I) has been significantly improved.

Embodiment 9: In Vivo PK Experiments

Assay materials: beagle dogs, three dogs per group, two groups in total (administered by compound 1-8 and crystal form A of the compound of formula (I) respectively)

Assay methods: the animals in each group were administered with corresponding compounds by orally gavage once, and blood samples were collected before and 2 h (±2 min), 4 h (±5 min), 6 h (±5 min), 8 h (±5 min), 12 h (±5 min), and 24 h (±10 min) after the administration. The samples were detected by LC-MS/MS, and AUC, $C_{max}$, and $T_{max}$ parameters were calculated by employing WinNonlin version 6.4.

Assay results: see Table 13.

TABLES 13

| Parameters | Compound I-8 | Crystal Form A of the compound of formula (I) |
|---|---|---|
| P.O. dose (mg/kg) | 300 | 300 |
| $C_{max}$ (nM) | 43467 | 75167 |
| $T_{max}$ (h) | 6 | 9.3 |
| $AUC_{0-last}$ (nM · h) | 613021 | 1309787 |
| $MRT_{0-last}$ (h) | 10.6 | 13.3 |

Assay conclusion: The crystal form A of the compound of formula (I) has good pharmacokinetic properties.

What is claimed is:
1. A compound of formula (I),

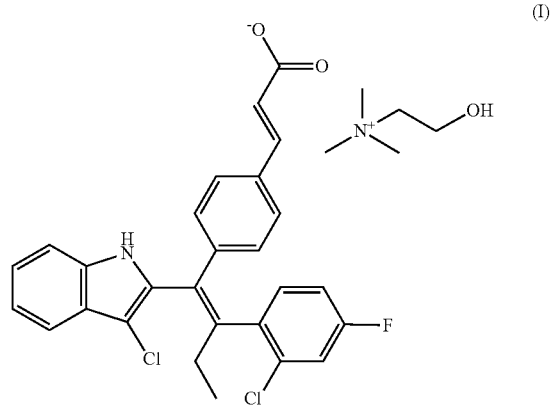

-continued (II)
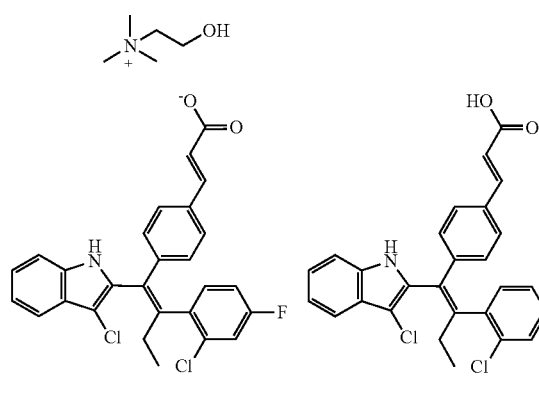

(III)
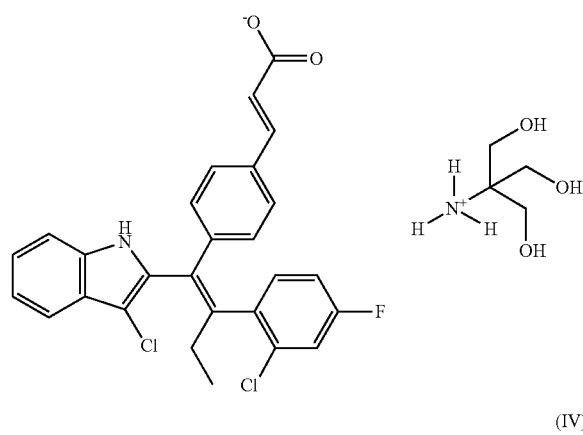

(IV)
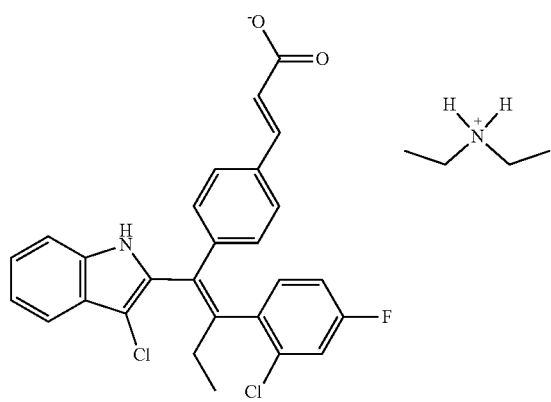

(V)
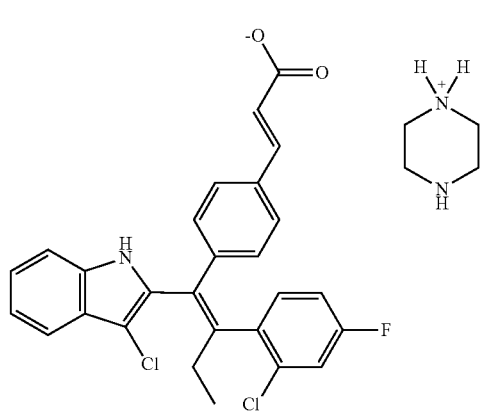

-continued (VI)
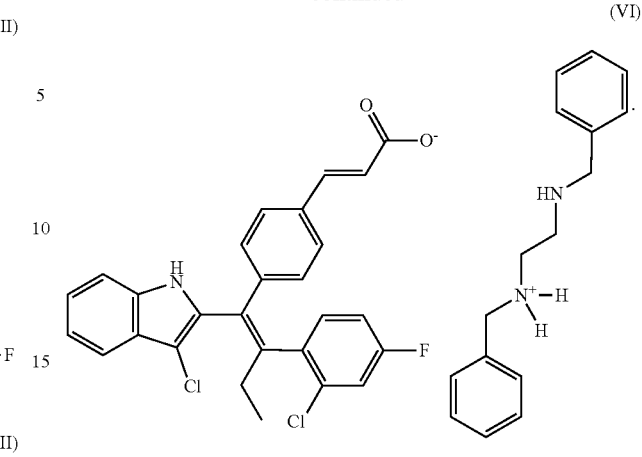

2. A crystal form A of the compound of formula (I) of claim 1, wherein the X-ray powder diffraction pattern under Cu-Kα radiation has characteristic diffraction peaks at the following 2θ angles: 5.52±0.2°, 13.68±0.2°, 19.98=0.2°, 20.80±0.2°, 22.02±0.2°, 22.44=0.2°, 24.94=0.2° and 26.96±0.2°, (I)
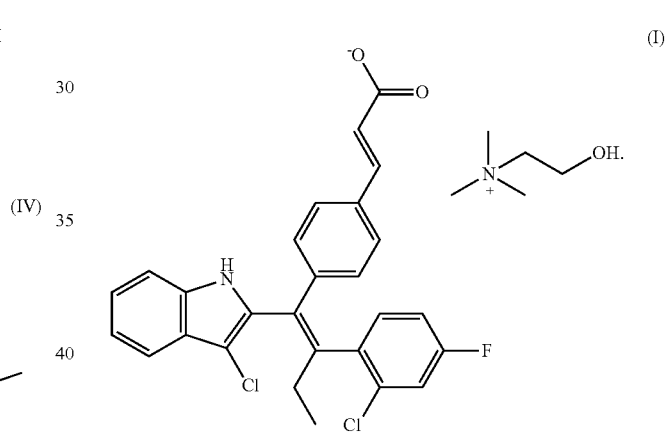

3. The crystal form A of the compound of formula (I) of claim 2, wherein the X-ray powder diffraction pattern under Cu-Kα radiation has nine or more than nine, ten or more than ten, or eleven or more than eleven characteristic diffraction peaks at the 2θ angles selected from the group consisting of 5.52±0.2°, 13.68±0.2°, 18.86±0.2°, 19.98±0.2°, 20.80±0.2°, 21.62=0.2°, 22.02=0.2°, 22.44=0.2°, 23.34=0.2°, 24.94=0.2°, 26.96±0.2° and 28.42±0.2°.

4. The crystal form A of the compound of formula (I) of claim 3, wherein the X-ray powder diffraction pattern under Cu-Kα radiation is shown in Table 1;

TABLE 1

| No. | 2θ Angle (°) | d-spacing (Å) | Intensity | Relative intensity (%) |
|---|---|---|---|---|
| 1 | 5.519 | 16.0002 | 891 | 84.0 |
| 2 | 10.023 | 8.8181 | 138 | 13.0 |
| 3 | 10.483 | 8.4319 | 169 | 15.9 |
| 4 | 10.962 | 8.0646 | 306 | 28.8 |
| 5 | 11.739 | 7.5328 | 259 | 24.4 |

TABLE 1-continued

| No. | 2θ Angle (°) | d-spacing (Å) | Intensity | Relative intensity (%) |
|---|---|---|---|---|
| 6 | 12.419 | 7.1213 | 283 | 26.6 |
| 7 | 13.68 | 6.468 | 581 | 54.7 |
| 8 | 15.401 | 5.7486 | 208 | 19.6 |
| 9 | 16.239 | 5.4539 | 114 | 10.8 |
| 10 | 16.973 | 5.2196 | 165 | 15.5 |
| 11 | 17.579 | 5.041 | 113 | 10.6 |
| 12 | 18.241 | 4.8596 | 194 | 18.3 |
| 13 | 18.859 | 4.7018 | 374 | 35.2 |
| 14 | 19.181 | 4.6234 | 201 | 18.9 |
| 15 | 19.979 | 4.4405 | 573 | 54.0 |
| 16 | 20.482 | 4.3327 | 598 | 56.4 |
| 17 | 20.802 | 4.2667 | 605 | 57.0 |
| 18 | 21.618 | 4.1075 | 373 | 35.1 |
| 19 | 22.019 | 4.0335 | 655 | 61.7 |
| 20 | 22.437 | 3.9593 | 1061 | 100.0 |
| 21 | 23.341 | 3.808 | 377 | 35.5 |
| 22 | 24.939 | 3.5676 | 413 | 38.9 |
| 23 | 25.957 | 3.4298 | 156 | 14.7 |
| 24 | 26.96 | 3.3045 | 755 | 71.1 |
| 25 | 27.561 | 3.2338 | 322 | 30.3 |
| 26 | 28.038 | 3.1798 | 202 | 19.0 |
| 27 | 28.419 | 3.138 | 409 | 38.5 |
| 28 | 29.454 | 3.0301 | 63 | 5.9 |
| 29 | 29.863 | 2.9895 | 98 | 9.2 |
| 30 | 30.459 | 2.9324 | 129 | 12.2 |
| 31 | 31.062 | 2.8769 | 123 | 11.5 |
| 32 | 31.638 | 2.8258 | 47 | 4.4 |
| 33 | 32.499 | 2.7528 | 186 | 17.5 |
| 34 | 33.841 | 2.6467 | 88 | 8.3 |
| 35 | 34.643 | 2.5872 | 36 | 3.4 |
| 36 | 35.035 | 2.5591 | 47 | 4.4 |
| 37 | 36.013 | 2.4918 | 42 | 3.4 |
| 38 | 37.44 | 2.4001 | 69 | 4.0 |
| 39 | 38.058 | 2.3625 | 93 | 6.5, | or, the differential scanning calorimetric curve has an endothermic peak at 239.46° C.±3° C.

5. A crystal form B of the compound of formula (I) of claim 1, wherein the X-ray powder diffraction pattern under Cu-Kα radiation has characteristic diffraction peaks at the following 2θ angles: 5.68±0.2°, 12.36±0.2°, 19.24±0.2°, 19.86±0.2°, 20.62±0.2°, 21.64±0.2°, 22.68±0.2° and 24.96=0.2°.

6. The crystal form B of the compound of formula (I) of claim 5, wherein the X-ray powder diffraction pattern under Cu-Kα radiation has nine or more than nine, ten or more than ten, or eleven or more than eleven characteristic diffraction peaks at the 2θ angles selected from the group consisting of 5.68±0.2°, 12.36±0.2°, 13.42±0.2°, 19.24±0.2°, 19.86±0.2°, 20.62±0.2°, 21.64±0.2°, 22.68±0.2°, 24.96±0.2°, 26.38±0.2°, 27.44=0.2° and 30.62±0.2°.

7. The crystal form B of the compound of formula (I) of claim 6, wherein the X-ray powder diffraction pattern under Cu-Kα radiation is shown in Table 2:

TABLE 2

| No. | 2θ Angle (°) | d-spacing (Å) | Intensity | Relative intensity (%) |
|---|---|---|---|---|
| 1 | 5.677 | 15.5537 | 459 | 73.3 |
| 2 | 9.756 | 9.0589 | 103 | 16.5 |
| 3 | 11.315 | 7.8134 | 53 | 8.5 |
| 4 | 12.363 | 7.1538 | 352 | 56.2 |
| 5 | 13.420 | 6.5923 | 315 | 50.4 |
| 6 | 14.798 | 5.9815 | 68 | 10.9 |
| 7 | 15.406 | 5.7470 | 41 | 6.6 |
| 8 | 16.481 | 5.3744 | 62 | 9.9 |
| 9 | 17.281 | 5.1273 | 128 | 20.5 |
| 10 | 17.721 | 5.0009 | 146 | 23.3 |
| 11 | 18.898 | 4.6920 | 253 | 40.5 |
| 12 | 19.239 | 4.6096 | 432 | 68.9 |
| 13 | 19.860 | 4.4668 | 481 | 76.7 |
| 14 | 20.619 | 4.3041 | 422 | 67.3 |
| 15 | 21.641 | 4.1032 | 626 | 100.0 |
| 16 | 22.681 | 3.9173 | 390 | 62.2 |
| 17 | 23.258 | 3.8213 | 98 | 15.6 |
| 18 | 24.959 | 3.5648 | 397 | 63.4 |
| 19 | 25.240 | 3.5257 | 222 | 35.4 |
| 20 | 26.378 | 3.3760 | 278 | 44.4 |
| 21 | 27.059 | 3.2926 | 66 | 10.6 |
| 22 | 27.438 | 3.2480 | 249 | 39.8 |
| 23 | 28.098 | 3.1732 | 79 | 12.6 |
| 24 | 28.482 | 3.1313 | 93 | 14.9 |
| 25 | 29.483 | 3.0272 | 66 | 10.6 |
| 26 | 30.002 | 2.9760 | 127 | 20.3 |
| 27 | 30.622 | 2.9171 | 267 | 42.6 |
| 28 | 31.080 | 2.8752 | 219 | 34.9 |
| 29 | 33.402 | 2.6804 | 41 | 6.6 |
| 30 | 34.198 | 2.6199 | 51 | 8.1 |
| 31 | 34.985 | 2.5627 | 79 | 12.7 |
| 32 | 38.698 | 2.3249 | 49 | 7.8 |
| 33 | 39.020 | 2.3065 | 67 | 10.6 |
| / | / | / | / | /. |

8. A method for treating breast cancer in a subject, comprising administering a therapeutically effective amount of the compound of formula (I) of claim 1 to the subject.

9. A method for treating breast cancer in a subject, comprising administering a therapeutically effective amount of the crystal form of claim 2 the subject.

10. A method for treating breast cancer in a subject, comprising administering a therapeutically effective amount of the crystal form of claim 5 to the subject.

* * * * *